(12) United States Patent
Feke

(10) Patent No.: US 8,724,979 B2
(45) Date of Patent: May 13, 2014

(54) IMAGING ENCLOSURE APPARATUS AND METHODS

(71) Applicant: Gilbert D. Feke, Windham, NH (US)

(72) Inventor: Gilbert D. Feke, Windham, NH (US)

(73) Assignee: Viewpoint Laboratories, LLC., Putnam, CT (US)

( * ) Notice: Subject to any disclaimer, the term of this patent is extended or adjusted under 35 U.S.C. 154(b) by 0 days.

(21) Appl. No.: 13/757,892

(22) Filed: Feb. 4, 2013

(65) Prior Publication Data

US 2014/0086567 A1    Mar. 27, 2014

Related U.S. Application Data

(60) Provisional application No. 61/706,529, filed on Sep. 27, 2012.

(51) Int. Cl.
*G03B 15/02* (2006.01)

(52) U.S. Cl.
USPC .............................. 396/4; 396/155

(58) Field of Classification Search
USPC ................................ 396/2–4, 155
See application file for complete search history.

(56) References Cited

U.S. PATENT DOCUMENTS

| RE25,167 | E   | * | 5/1962  | Booth et al. ............... 396/360 |
| 3,774,046 | A  |   | 11/1973 | Hoch et al. |
| 4,657,655 | A  |   | 4/1987  | Smoot et al. |
| 6,775,567 | B2 | * | 8/2004  | Cable et al. ............... 600/407 |
| 7,016,551 | B1 | * | 3/2006  | Abe et al. .................. 382/284 |
| 7,253,838 | B2 | * | 8/2007  | Oliver ....................... 348/345 |
| 7,783,178 | B2 | * | 8/2010  | Liu ............................. 396/4 |
| 7,877,003 | B2 | * | 1/2011  | Dunn et al. .................. 396/4 |
| 7,978,970 | B2 | * | 7/2011  | Pastore ...................... 396/155 |
| 2005/0002069 | A1 | * | 1/2005 | Schnitzlein et al. ........ 358/483 |
| 2008/0062263 | A1 | * | 3/2008 | Shiu et al. .................. 348/96 |
| 2008/0137325 | A1 | * | 6/2008 | Pastore ....................... 362/16 |
| 2008/0170380 | A1 | * | 7/2008 | Pastore ....................... 362/16 |

* cited by examiner

*Primary Examiner* — Clayton E LaBalle
*Assistant Examiner* — Warren K Fenwick
(74) *Attorney, Agent, or Firm* — Louis S. Horvath

(57) ABSTRACT

An imaging apparatus for imaging an object has an enclosure chassis that defines an enclosed imaging volume and that provides an imaging aperture to a camera apparatus that mounts against the chassis and that further provides at least a first lateral access opening for access to the object. A light-obstructing gasket is coupled to the enclosure chassis and has at least a first foldable lateral access leaf that folds to a first position against the first lateral access opening to block ambient light through the first lateral access opening and that folds away from the first lateral access opening to a second position to allow access to the object.

20 Claims, 31 Drawing Sheets

IMAGING ENCLOSURE APPARATUS AND METHODS

CROSS REFERENCE TO RELATED APPLICATION

Priority is claimed from commonly assigned, provisional U.S. patent application Ser. No. 61/706,529 filed Sep. 27, 2012 by Gilbert D. Feke for MOBILE DEVICE IMAGING SYSTEM AND METHOD, the contents of which are incorporated herein by reference.

FIELD OF THE INVENTION

The present invention relates generally to imaging systems and more particularly to apparatus and methods related to enclosures adapted for imaging enclosed objects.

BACKGROUND OF THE INVENTION

Enclosures have been adapted for imaging objects under controlled illumination. One type of conventional enclosure has an opaque barrier whose purpose is to partially or totally separate light related to the imaging activity inside the enclosure from ambient light unrelated to the imaging activity outside the enclosure. Such enclosures may provide additional utility for the imaging activity. An example of a known enclosure with an opaque barrier for totally separating light inside the enclosure from light outside the enclosure is a hood. Such a hood typically comprises an opaque material, for example metal or plastic, that encompasses and defines a volume for containing an object to be imaged; a first opening formed for abutting the hood to a platform for supporting the object to be imaged; a second opening formed for exposing the object to an imaging device, for example a camera; and a fixture for mounting the imaging device in a position that enables the imaging device to image the object. The first and second openings are typically formed to serve their respective functions while preserving the integrity of the barrier, for example by employing compressible light-tight gaskets capable of providing a light barrier at the physical interfaces between the openings and components in physical contact with the openings. For example, in U.S. Pat. No. 4,657,655 which describes an apparatus for electrophoretically separating, visualizing and photographing DNA fragments in agarose gels, a camera assembly includes a hood which serves the primary purpose of light separation. The hood blocks ambient light and isolates the light related to the imaging activity inside the enclosure. In this example this is ultraviolet light from a transilluminator used for exciting ethidium bromide-stained DNA fragments and the resultant fluorescence light from the excited DNA fragments, detected by an instant film camera. Such separation is necessary because the ambient light would otherwise compromise imaging of the DNA fragments by adding unwanted background signal to the image. Further, it is desirable to shield an operator of such an apparatus from ultraviolet light which would otherwise escape into the immediate surroundings of the apparatus. Additionally the hood serves a secondary purpose as a positioning mechanism for configuring the instant film camera in an optimal spatial relationship with respect to the agarose gel supported by the transilluminator, as well as serving other purposes, such as providing a mechanism for activating a switch for fluorescent lamps in the transilluminator when the camera is properly placed thereupon.

In one known hood implementation, the barrier is continuous so that the object must be placed upon the platform first, and then the hood must be placed upon the platform, such that the hood encloses the object, thereby completing the barrier for imaging activity. This implementation has significant ergonomic limitations, since repeated placement and removal of the hood is necessary for sequentially imaging multiple objects.

In another known implementation of a hood, the barrier has a hatch door positioned in a front area of the enclosure facing an operator. This allows the operator to view inside the enclosure and insert an object along the viewing perspective. The hood can be placed upon the platform first, or even permanently, and then the hatch door can be opened for inserting the object and viewing the insertion of the object. The hood is finally closed for completing the barrier for imaging activity. Although the hatch door provides some improvement over the continuous barrier, this implementation is still subject to ergonomic limitations; it is often desirable for an operator of such apparatus to have unilateral or bilateral access to the void or volume into which the object is placed, for example to use one hand on one side, or two hands with one on each side for positioning, while viewing from the front area of the enclosure. Further, in the case where the hatch door is not removable from the enclosure, the hatch door requires clearance space for it to occupy in the open position. For example, if the hatch door opens by means of a hinge, the hatch door would typically open outward so that it occupies space exterior to the enclosure when in the open position. This is an inconvenience, although it may be preferable to having the hatch door open inward into the imaging area where it could interfere with the enclosed object. Alternately, if the hatch door opens using a slide rail, additional space is required to allow movement of the hatch door into a recess in the enclosure. The enclosure would need to be elongated in the direction of the slide rail to provide such a recess beyond the space required to enclose the object. Further, in the case where the hatch door is removable from the enclosure, then the hatch door requires accommodation for storage when removed.

Another example of a known enclosure comprising an opaque barrier for separating light inside the enclosure from light outside the enclosure is a box. Such a box typically is formed using an opaque material, for example metal or plastic, that encompasses a volume containing an object to be imaged. A platform is integral or enclosed within the enclosure for supporting the object to be imaged. An aperture is formed for exposing the object to an imaging device, for example a camera. A fixture is provided for mounting the imaging device in a position that enables the imaging device to image the object. The device also has a door. The opening is typically formed to serve its function while preserving the integrity of the barrier, for example by employing compressible gaskets capable of providing a light barrier at the physical interface between the opening and components in physical contact with the opening. Further the door is typically formed to serve its function while preserving the integrity of the barrier when closed. Examples of imaging boxes are described in U.S. Pat. No. 6,775,567.

In one known implementation of a box, the door is positioned in a front area of the enclosure facing an operator, for the operator to both view inside the enclosure and insert an object along the viewing perspective. This implementation can be difficult to work with, since it is often desirable for an operator of such apparatus to have unilateral or bilateral access to the volume into which the object is placed, for example to use one hand on one side, or two hands with one on each side, while viewing from the front area of the enclosure. Further, in the case where the door is not removable from the enclosure, the door undesirably requires space for it to occupy in the open position. For example, if the door opens by means of a hinge, the door would typically open outward so that it occupies space exterior to the enclosure in the open position, which is an inconvenience albeit preferred over the door opening inward into the volume where it could interfere with the enclosed object. Alternately, if the door opens by means of a slide rail providing movement of the door into a recess in the enclosure, then the enclosure would undesirably need to be elongated in the direction of the slide rail to provide such a recess beyond the space required to enclose the object. Further, in the case where the door is removable from the enclosure, then the door undesirably requires accommodation for storage when removed.

Another example of a known enclosure comprising an opaque barrier for partially separating light inside the enclosure from light outside the enclosure is a slotted box. Such a slotted box is similar to the hood or box type enclosures described above, but provides a permanent opening for ergonomic insertion and removal of objects to be imaged, thereby obviating the need for removing and replacing the enclosure with respect to a platform or opening and closing a door. For example U.S. Pat. No. 3,774,046, related to a detector of counterfeit currency, describes such a box having a slot. Although the slot in U.S. Pat. No. 3,774,046 is formed to provide bilateral access to the volume into which the object is placed, for example to use two hands with one on each side, while viewing from the front area of the enclosure, a means for completely separating light inside the enclosure from light outside the enclosure is not provided.

The platform for supporting the object to be imaged in known implementations of hood, box and slotted box enclosures is typically configured to be normal to a gravitational field so that the object is held in place by the force of gravity. The opening formed to expose the object to the imaging device in known implementations of hood, box and slotted box enclosures is typically substantially opposed to the platform for supporting the object so as to provide a direct line of sight for the imaging device to the object. Hence, the platform for supporting the object is typically located at the bottom of the enclosure and the imaging device is typically located at the top of the enclosure. The fixture for mounting the imaging device in known implementations of hood, box and slotted box enclosures typically provides rigid mounting of a camera or other type of imaging device.

In one example of known imaging systems that include hood, box or slotted box enclosures, the imaging system includes an imaging device, such as a camera, and a separate display that is not integral to the imaging device. This display can be a computer monitor, for example, for viewing image data from the imaging device, as described in U.S. Pat. No. 6,775,567. In this example, the separate display provides an ergonomic advantage, as it may be positioned for viewing by an operator independent of the location of the imaging system and imaging device. However, such known imaging systems are subject to a limitation in that if the imaging device happened to include an on-board display integral to the device, as is common with state-of-the-art mobile devices such as smartphone devices, tablet devices and point-and-shoot digital camera devices, then the separate display would be redundant and hence add undesirable cost and complexity to the system. It would generally be advantageous if such imaging systems that included imaging devices with integral displays did not require separate displays for viewing image data from the imaging device. However, since the fixture for mounting the imaging device in known implementations of hood, box and slotted box enclosures typically provides rigid mounting, and since the imaging device is typically located at the top of the enclosure, the only options for the operator of such systems for viewing the captured image or image data on a display integral to the imaging device are either to view from above the imaging device or to remove the device. Viewing the captured image from above the device often requires the operator to be in an uncomfortable position because the imaging system is often located on a workbench and the enclosure is required to be sufficiently tall to enable the imaging device to focus on the object with a sufficiently large field of view. Removal of the imaging device from the fixture allows viewing the image data in a more comfortable position; however, removal of the imaging device is often undesirable because of the effort required to remove the imaging device and then reinstall it at a later time. Hence, it would be desirable to have an imaging device with an integral display that is more readily viewable.

Examples of methods related to such enclosures include those related to counterfeit article detection, for example evaluation of the authenticity of banknotes, driver's licenses, passports, credit cards, bank checks, casino tokens, pill bottles, etc. Conventional detection methods typically require an operator to view the object within the enclosure and, either using memory or at best referring to a printed reference book, to make a judgment of the authenticity of the object. Due to the lack of adaptations of known enclosures for mobile devices, such methods are subject to limitations of not being able to readily use the features common in state-of-the-art mobile devices, such as imaging, computing power capable of pattern recognition, display, the ability to retrieve information from a remote server via a telecommunications network, and instant printing. It would be desirable for such methods to take advantage of the features of mobile devices.

SUMMARY OF THE INVENTION

The present invention addresses the aforementioned limitations of conventional imaging apparatus by providing apparatus and methods related to imaging at least one enclosed object. According to one aspect of the present invention, there is provided an imaging apparatus for imaging an object, the imaging apparatus comprising:

an enclosure chassis that defines an enclosed imaging volume and that provides an imaging aperture to a camera apparatus that mounts against the chassis and that further provides at least a first lateral access opening for access to the object;
and
a light-obstructing gasket that is coupled to the enclosure chassis and that has at least a first foldable lateral access leaf that folds to a first position, against the first lateral access opening to block ambient light through the first lateral access opening, and that folds away from the first lateral access opening to a second position to allow access to the object.

The imaging apparatus separates light inside the enclosed imaging volume from ambient light, unrelated to the imaging activity, outside the enclosed imaging volume. The enclosed imaging volume is capable of containing at least one enclosed object. The imaging apparatus further has a surface for providing support for the at least one enclosed object. The surface may be an integral interior surface or otherwise enclosed within the enclosure chassis. Alternately, the surface may be separate from the enclosure chassis and further provide support for the enclosure chassis having an opening formed for abutting the enclosure chassis to the surface. The camera apparatus has integral optics and imaging sensing mechanism positioned on a rear surface of the camera apparatus. The camera apparatus may further comprise an integral display, for viewing images acquired by the camera apparatus, positioned on a front surface of the camera apparatus. The integral display may comprise a touch screen control interface. The surface for providing support for the at least one enclosed object may comprise a platform having a light source that is energizable for illuminating the enclosed imaging volume through an illumination opening in the enclosure chassis. The light-obstructing gasket may further obstruct light entry between the enclosure chassis and the platform. The imaging apparatus may further comprise one or more enclosed light sources. The one or more enclosed light sources may be positioned to illuminate the at least one enclosed object from the same side as the camera apparatus. The one or more enclosed light sources may comprise at least two enclosed light sources wherein the at least two enclosed light sources comprise different wavelength profiles. The light-obstructing gasket may be formed from a compressible material. The enclosure chassis may further provide a second lateral access opening for access to the object and the light-obstructing gasket may further comprise a second foldable lateral access leaf that folds removably against the second access opening. At least one foldable lateral access leaf may lie against the surface for supporting the enclosure chassis when in the second position. At least one foldable lateral access leaf may be magnetically attracted to the first position against the first lateral access opening. The enclosure chassis may further include at least one magnetic or ferromagnetic member and at least one foldable lateral access leaf may include at least one magnetic member for magnetic attachment to the at least one magnetic or ferromagnetic member of the enclosure chassis. Alternately, at least one foldable lateral access leaf may include at least one magnetic or ferromagnetic member and the enclosure chassis may further include at least one magnetic member for magnetic attachment to the at least one magnetic or ferromagnetic member of the at least one foldable lateral access leaf. The at least one foldable lateral access leaf may further comprise one or more stiffener elements that are formed from a magnet or from a ferromagnetic material. The second position may comprise a removed position wherein the light-obstructing gasket is removed from the enclosure chassis. The first and second lateral access leaves may comprise two bilaterally opposed lateral access leaves. The surface for supporting the enclosure chassis may comprise a ferromagnetic member and the light-obstructing gasket may further comprise at least one magnetic member for magnetic attachment of the light-obstructing gasket to the surface. The enclosure chassis may further comprise a front viewport enabling viewing of the at least one enclosed object from the front of the enclosure chassis, wherein the front viewport may be selectively obstructed by an obstruction such as an additional light-obstructing gasket. The imaging apparatus may comprise one or more hinge elements that allow pivoting of the camera apparatus against or away from a surface of the enclosure chassis, for example for increasing the comfort related to viewing an image of the object on the integral display or for aiding the docking or undocking of the camera apparatus from the fixture. The one or more hinge elements may comprise one or more friction hinges. The imaging apparatus may further comprise a receiving member sized and shaped to conform to the camera apparatus. The receiving member may comprise a case. The case may include a lockable security case. The imaging apparatus may further include a mirror, internal to the enclosure chassis, for folding an imaging path of the camera apparatus. The surface for supporting the at least one object may further include at least one illumination indicator within a field of view of the camera apparatus, wherein the at least one illumination indicator is interpretable by the camera apparatus for determining whether the at least one enclosed light source is energized.

The present invention further relates to methods of using a counterfeit article detection apparatus adapted for mobile devices. One exemplary method has a series of steps. A first step of the series of steps includes positioning at least one object in a field of view of a camera integral to a mobile device. For example, the at least one object may be a banknote, driver's license, passport, credit card, a check, casino token, or pill bottle, and include both a reproduced artwork printed using ink visible under visible illumination such as white light, and either the presence or absence of a fluorescent authentication substance, such as fluorescent artwork or a fluorescent strip, visible by means of fluorescence under ultraviolet illumination. Optionally, at least one illumination indicator may also be positioned within the field of view of the camera alongside the at least one object. A second step of the series of steps comprises illuminating the at least one object, and optionally the at least one illumination indicator, with visible illumination such as white light. A third step of the series of steps comprises imaging the at least one object, and optionally the at least one illumination indicator, under visible illumination with the camera. An optional fourth step of the series of steps comprises interpreting the illumination indicator to achieve an interpretation result corresponding to visible illumination, wherein the interpretation is automatically achieved by an image processor, for example integral to either the mobile device or a remote server. A fifth step of the series of steps comprises recognizing the at least one object by means of image recognition, wherein the recognizing may be by the naked eye or alternately automatically achieved by the image processor by means of the interpretation result. An optional sixth step of the series of steps comprises simultaneously displaying a current reflectance image of the at least one object and a reference reflectance image of the at least one object, wherein the reference image is retrieved from an archive by means of triggering a retrieval sequence based on the recognizing of the at least one object. A seventh step of the series of steps comprises illuminating the at least one object, and optionally the at least one illumination indicator, with ultraviolet illumination to enable the at least one object, and optionally the at least one illumination indicator, to fluoresce, wherein the at least one object fluoresces if the fluorescent substance is present. An eighth step of the series of steps comprises imaging the at least one object, and optionally the at least one illumination indicator, under the ultraviolet illumination with the camera. An optional ninth step of the series of steps comprises interpreting the at least one illumination indicator to achieve an interpretation result corresponding to ultraviolet illumination, wherein the interpretation is automatically achieved by an image processor. An optional tenth step of the series of steps comprises recognizing the at least one object by means of image recognition, wherein the recognizing may be by the naked eye or alternately automatically achieved by the image processor by means of the interpretation result. An optional eleventh step of the series of steps comprises simultaneously displaying a current fluorescence image of the at least one object and a reference fluorescence image of the at least one object, wherein the reference image is retrieved from an archive by means of triggering a retrieval sequence based on the recognizing of the at least one object. An optional twelfth step of the series of steps comprises judging the authenticity of the at least one object by comparing the current fluorescence image of the at least one object against the reference fluorescence image of the at least one object, wherein the judging may be by the naked eye or automatically achieved by the image processor. An optional thirteenth step of the series of steps comprises informing an operator of the counterfeit article detection system regarding the authenticity, or lack thereof, of the at least one object, wherein the informing may be visible, audible, haptic, or any combination thereof.

These and other objects, features, and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures.

DETAILED DESCRIPTION OF THE INVENTION

Reference will now be made in detail to exemplary embodiments of the present invention, examples of which are illustrated in the accompanying drawings. Wherever possible, the same reference numbers will be used throughout the drawings to refer to the same or like parts. While the description includes exemplary embodiments, other embodiments are possible and changes may be made to the embodiments described without departing from the spirit and scope of the invention. The following detailed description does not limit the invention.

In the context of the present disclosure, terms "top" and "bottom" or "above" and "below" are relative and do not indicate any necessary orientation of a component or surface, but are used simply to refer to and distinguish opposite surfaces or relative spatial relationships of components. Similarly, terms "horizontal" and "vertical" may be used relative to the figures, to describe the relative orthogonal relationship of components, for example, but do not indicate any required orientation of components with respect to true horizontal and vertical orientation.

Where they are used, the terms "first", "second", "third", and so on, do not necessarily denote any ordinal or priority relation, but are used for more clearly distinguishing one element or time interval from another. For example, there are no fixed "first" or "second" elements in what is taught herein; these descriptors are merely used to clearly distinguish one element from another similar element in the context of the present disclosure.

As used herein, the term "energizable" relates to a device or set of components that perform an indicated function upon receiving power and, optionally, upon receiving an enabling signal. For example, a light source is energizable to emit light. The term "magnetizable" indicates that a material is attracted and held by magnetic force; "magnetizable material" includes ferromagnetic materials.

Figure 1:
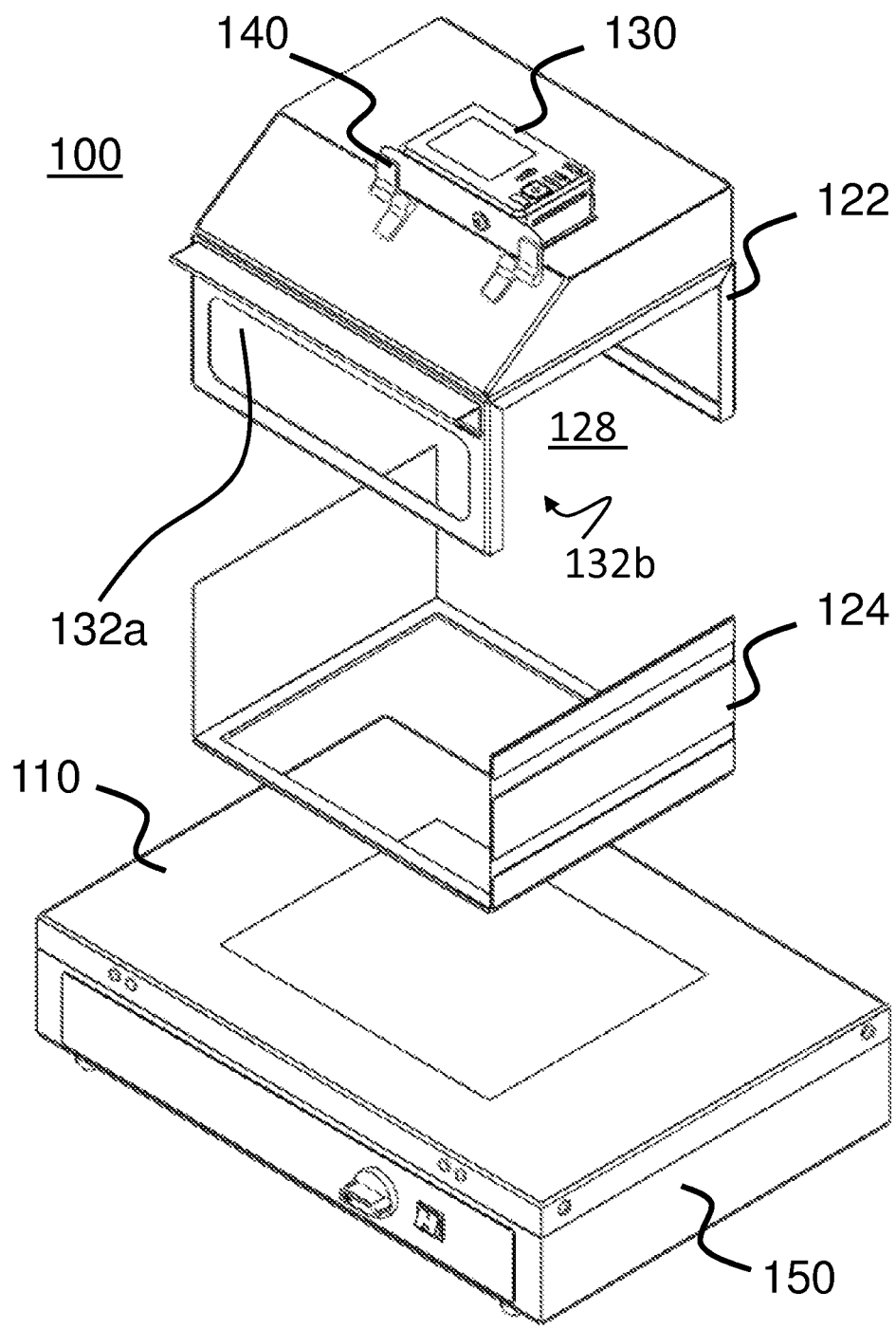
FIG. 1 shows an exploded perspective view of an imaging apparatus, consistent with an embodiment of the present invention, comprising a platform; an enclosure chassis and a light-obstructing gasket; and a camera apparatus mounted upon the enclosure chassis, by a fixture, and positioned in a first position for abutting the camera apparatus to an opening formed in the enclosure chassis.

FIG. 1 shows an exploded view of imaging apparatus 100, consistent with an embodiment of the present invention, comprising: a platform 110; an enclosure chassis 122 and a first light-obstructing gasket 124 that is coupled to enclosure chassis 122; and a camera apparatus 130 mounted upon enclosure chassis 122 by means of a hinged arrangement or fixture 140. A platform 110 is integral to a transilluminator 150 that provides light, for example ultraviolet light (having wavelengths from about 250 nm to about 380 nm), visible light (having wavelengths from about 380 nm to about 750 nm) such as blue or white light, or near-infrared light (having wavelengths from about 750 nm to about 1100 nm), for transillumination. According to an embodiment of the present invention, camera apparatus 130 uses a point-and-shoot camera device. One of ordinary skill in the art can appreciate that camera apparatus 130 may alternately be another type of imaging device such as an image capture apparatus that is integral to a mobile device such as a smartphone or tablet device, or more generally any type of imaging device suitable for use in conjunction with the other components of the apparatus. Camera apparatus 130 has features known to one of ordinary skill in the art including integral camera optics and an image sensing mechanism, such as a CMOS (Complementary Metal Oxide Semiconductor) or CCD (Charge-Coupled Detector) digital sensor array or using a photosensitive medium such as camera film, positioned on a rear surface of camera apparatus 130, and an integral display, for viewing images acquired by camera apparatus 130, positioned on a front surface of camera apparatus 130. The integral display may have a touch screen control interface. Camera apparatus 130 is shown positioned in a first position for abutting camera apparatus 130 to an imaging aperture (not shown in FIG. 1) in enclosure chassis 122. First light-obstructing gasket 124 may be formed from a compressible material, such as polyurethane foam.

As shown in FIG. 1, enclosure chassis 122 defines an enclosed imaging volume 128. As described in more detail subsequently, first light-obstructing gasket 124 is configured to either block ambient light from imaging volume 128 or to allow access to an object within imaging volume 128 for insertion, removal, or adjusting its position. First light-obstructing gasket 124 further obstructs light entry for a gap between the enclosure chassis 122 and the platform 110.

Figure 2:
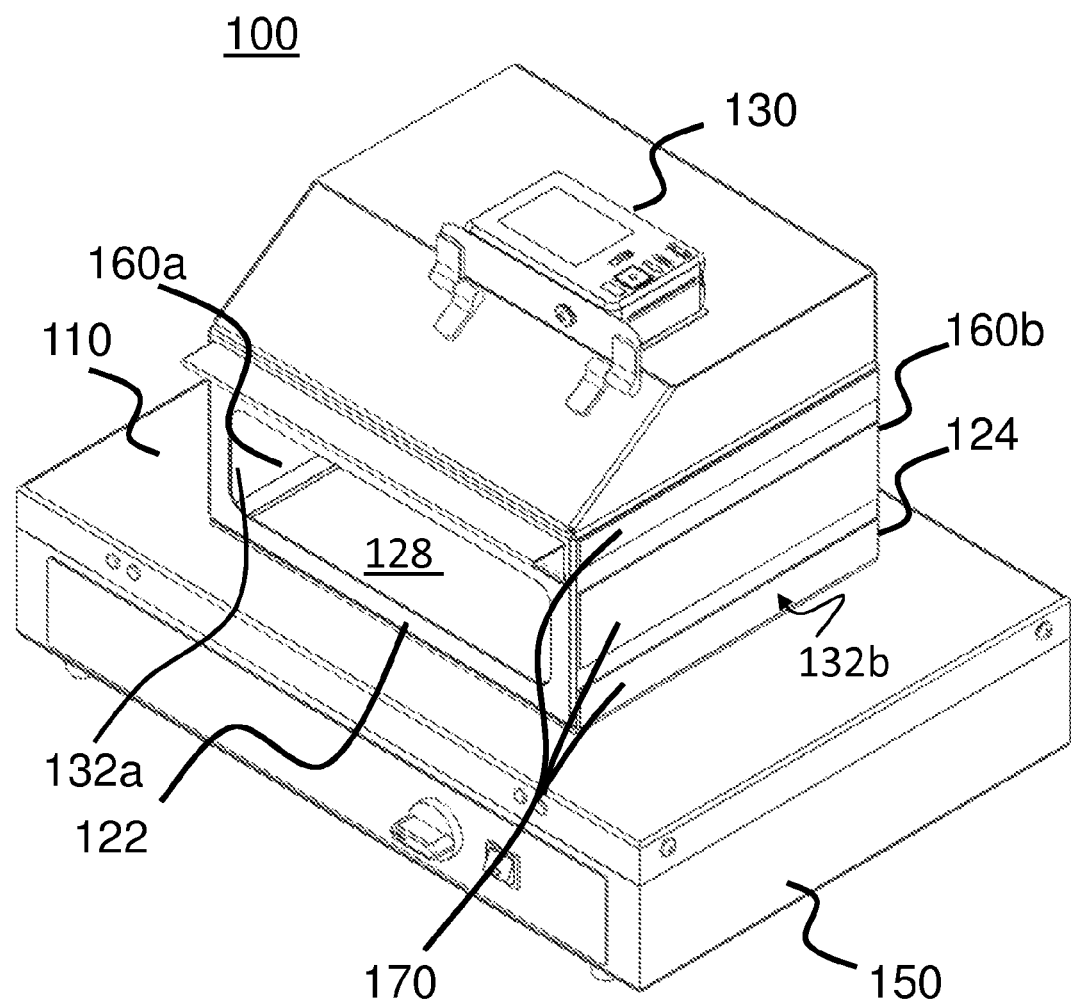
FIG. 2 shows a perspective view of the imaging apparatus of FIG. 1 in an assembled state.

FIG. 2 shows a perspective view of imaging apparatus 100 of FIG. 1 in an assembled state. The assembly procedure may include first, placing first light-obstructing gasket 124 onto platform 110, and second, placing enclosure chassis 122 onto first light-obstructing gasket 124. Alternately, the assembly may include first, attaching first light-obstructing gasket 124 to enclosure chassis 122 to form a subassembly and second, placing the subassembly onto platform 110. The opacity of enclosure chassis 122 allows separation of light related to an imaging activity inside imaging volume 128 from ambient light from outside imaging volume 128 that is unrelated to the imaging activity. Enclosure chassis 122 is formed to define imaging volume 128 capable of containing at least one enclosed object and platform 110 is for providing support for the at least one enclosed object. Platform 110 further provides support for enclosure chassis 122 having a second opening formed for abutting enclosure chassis 122 to platform 110. Optional transilluminator 150 is for illuminating the at least one object from behind with respect to camera apparatus 130. One of ordinary skill in the art can appreciate that the platform may alternately not provide illumination, for example the platform may be a simple plate. One of ordinary skill in the art can further appreciate that imaging apparatus 100 may optionally further comprise at least one light source positioned to illuminate the at least one object from the same side as the imaging device, wherein the at least one light source may be separate from camera apparatus 130. The light source may be a lamp, for example, or may be integral to camera apparatus 130, such as a flash element of camera apparatus 130. One of ordinary skill in the art can further appreciate that the platform may either include a flat surface or alternately comprise a non-flat surface such as a curved or non-uniform surface. First light-obstructing gasket 124 provides a light-obstructing interface between enclosure chassis 122 and platform 110. Platform 110 has a ferromagnetic surface, such as steel, and first light-obstructing gasket 124 has at least one magnetic member for magnetic attachment of first light-obstructing gasket 124 to platform 110. One of ordinary skill in the art can appreciate that the platform may alternately include a nonmagnetizable surface and enclosure chassis 122 and first light-obstructing gasket 124 may be held in place with respect to the platform by simple gravity. First light-obstructing gasket 124 has two bilaterally opposed integral foldable lateral access leaves 160a and 160b shown folded to a closed position, against and blocking lateral access openings 132a and 132b, respectively, for complementing the opacity of imaging apparatus 100 in conjunction with enclosure chassis 122. One of ordinary skill in the art can appreciate that the first light-obstructing gasket may alternately comprise a single integral foldable lateral access leaf. Enclosure chassis 122 is formed from a ferromagnetic material, such as steel, and foldable lateral access leaves 160a and 160b are each comprised of a set of magnetic panels 170 attached, for example by an adhesive layer, to the compressible material of first light-obstructing gasket 124, such that in the closed position set of magnetic panels 170 are on the opposite side of first light-obstructing gasket 124 as enclosure chassis 122 and hence magnetically attracted to enclosure chassis 122 through first light-obstructing gasket 124 such that a compressing force is applied by set of magnetic panels 170 to compress first light-obstructing gasket 124 to enclosure chassis 122 to both support foldable lateral access leaves 160a and 160b in the closed position and to reinforce the integrity of first light-obstructing gasket 124 against light. One of ordinary skill in the art can appreciate that the enclosure chassis may alternately be formed from a magnetic material and the foldable lateral access leaves may each have ferromagnetic panels and achieve the same function. The magnetic or ferromagnetic panels 170 attached to foldable lateral access leaves 160a and 160b may further serve as stiffener elements to stiffen segments of the foldable lateral access leaves 160a and 160b.

According to an alternate embodiment of the present invention, conventional fasteners such as hook-and-loop or hook-and-hook fasteners, resealable adhesive, zipper, snap, turnscrew, or similar fastener are used instead of magnetic attraction for securing leaves 160a and 160b against enclosure chassis 122.

Figure 3:
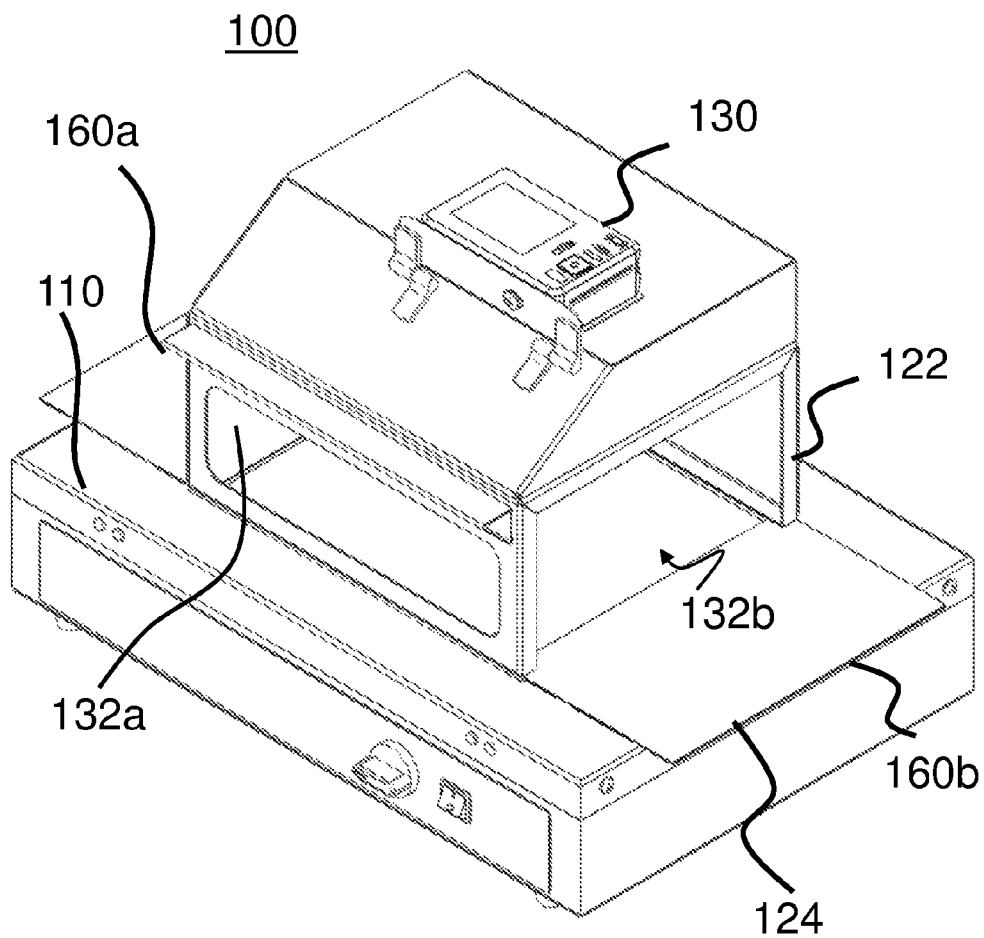
FIG. 3 shows the imaging apparatus of FIG. 2 with foldable lateral access leaves folded down to conform to the platform.

FIG. 3 shows imaging apparatus 100 of FIG. 2 with foldable lateral access leaves 160a and 160b folded to an open position, away from lateral access openings 132a and 132b, respectively, folded down to conform to platform 110, for providing access from the sides of enclosure chassis 122 for object access. The open position is orthogonal to the closed position. This allows placing the at least one object onto the platform inside enclosure chassis 122 so that no impediment is presented to the side access of enclosure chassis 122 and the space required for maintaining the foldable lateral access leaves 160a and 160b in the open position is minimized. Foldable lateral access leaves 160a and 160b, folded down to conform to platform 110, provide an ergonomic advantage such as for an operator armrest on folded down leaves 160a and 160b while the operator works with the enclosed object and accesses the object from different sides of enclosure chassis 122.

Figure 4:
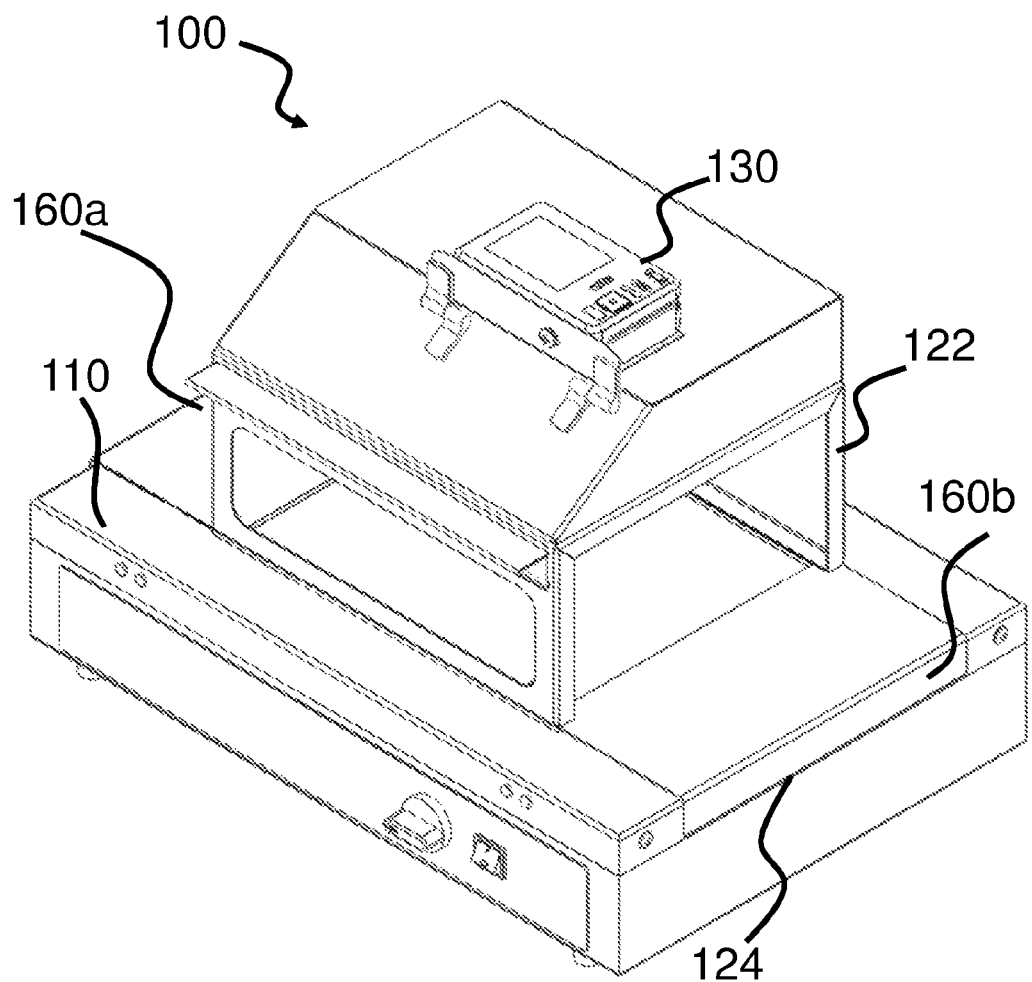
FIG. 4 shows the imaging apparatus of FIG. 3 with the foldable lateral access leaves further draped over the edges of the platform.

FIG. 4 shows imaging apparatus 100 of FIG. 3 with movable lateral access leaves 160a and 160b further draped over the edges of platform 110. The draping over an edge of platform 110 may be achieved by means of an arrangement of the set of magnetic or ferromagnetic panels of the leaves such that a gap between two separate panels aligns with the edge of the platform, thus allowing first light-obstructing gasket 124 to be creased within the gap by the edge of platform 110. Gaps between separate panels may further serve the purpose of enabling first light-obstructing gasket 124 to be draped over platforms of different sizes.

Figure 5:
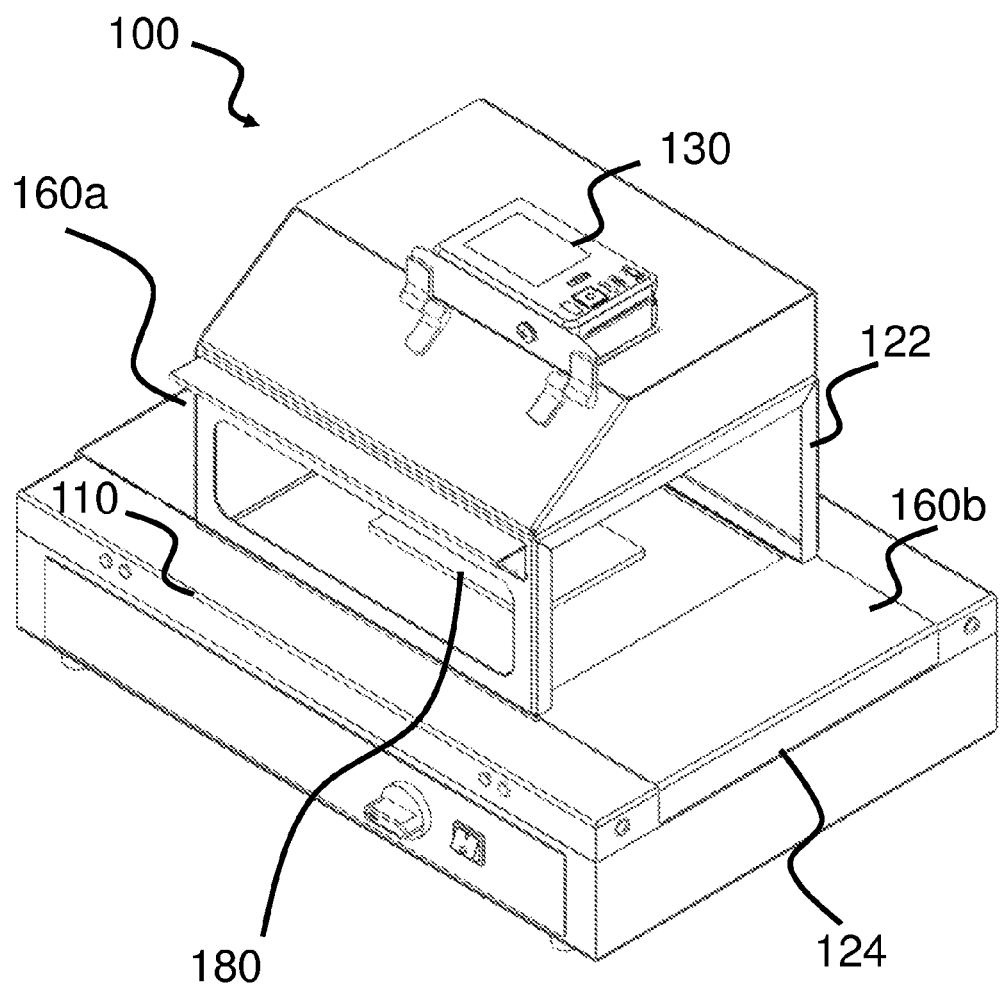
FIG. 5 shows the imaging apparatus of FIG. 4 with an object inserted into the enclosure chassis and placed atop the platform.

FIG. 5 shows imaging apparatus 100 of FIG. 4 with an enclosed object 180 having been inserted into enclosure chassis 122 and placed atop platform 110 such that object 180 is positioned within a field of view of camera apparatus 130. Enclosed object 180 can be an agarose gel, as used for gel electrophoresis, for example. Generally, enclosed object 180 may be any imagable object that fits inside the enclosure chassis.

Figure 6:
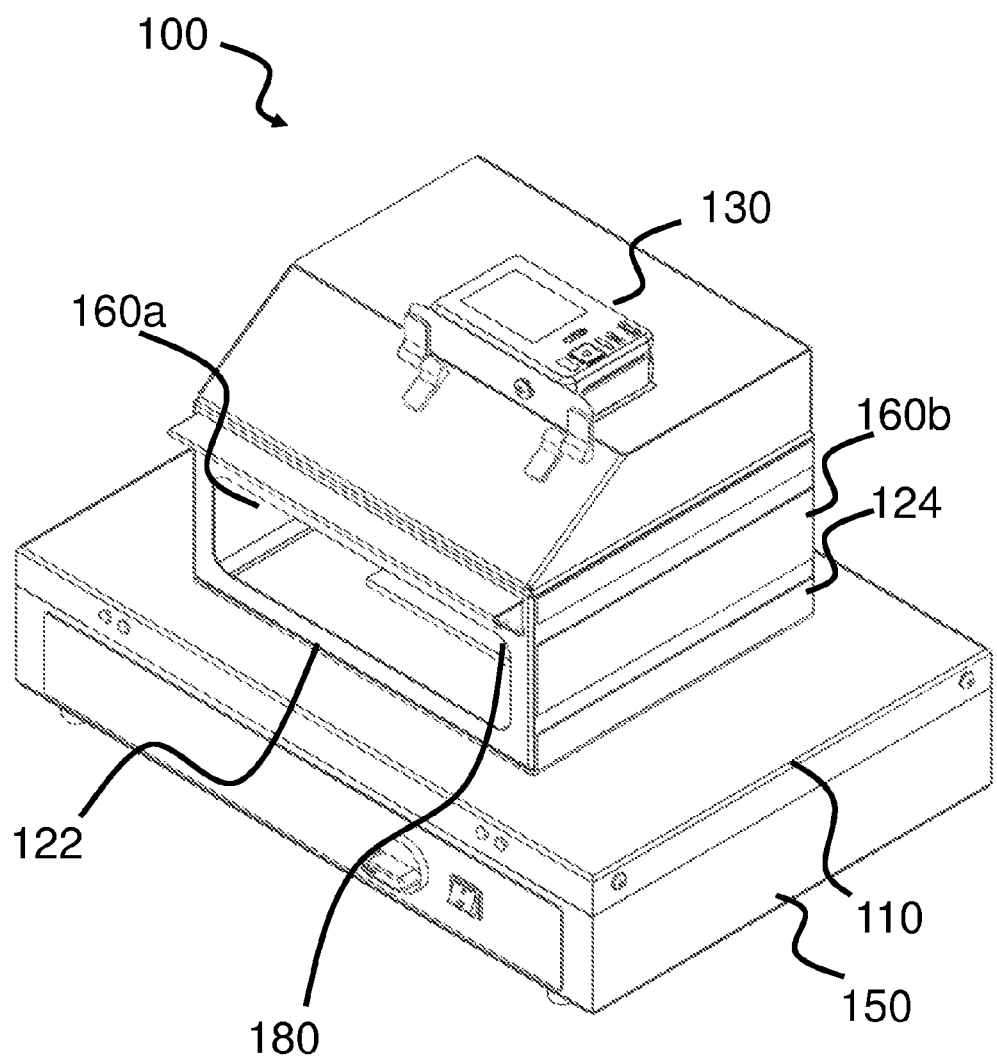
FIG. 6 shows the imaging apparatus of FIG. 5 with the foldable lateral access leaves reclosed.

FIG. 6 shows imaging apparatus 100 of FIG. 5 with foldable lateral access leaves 160a and 160b reclosed following insertion or adjustment of object 180.

Figure 7:
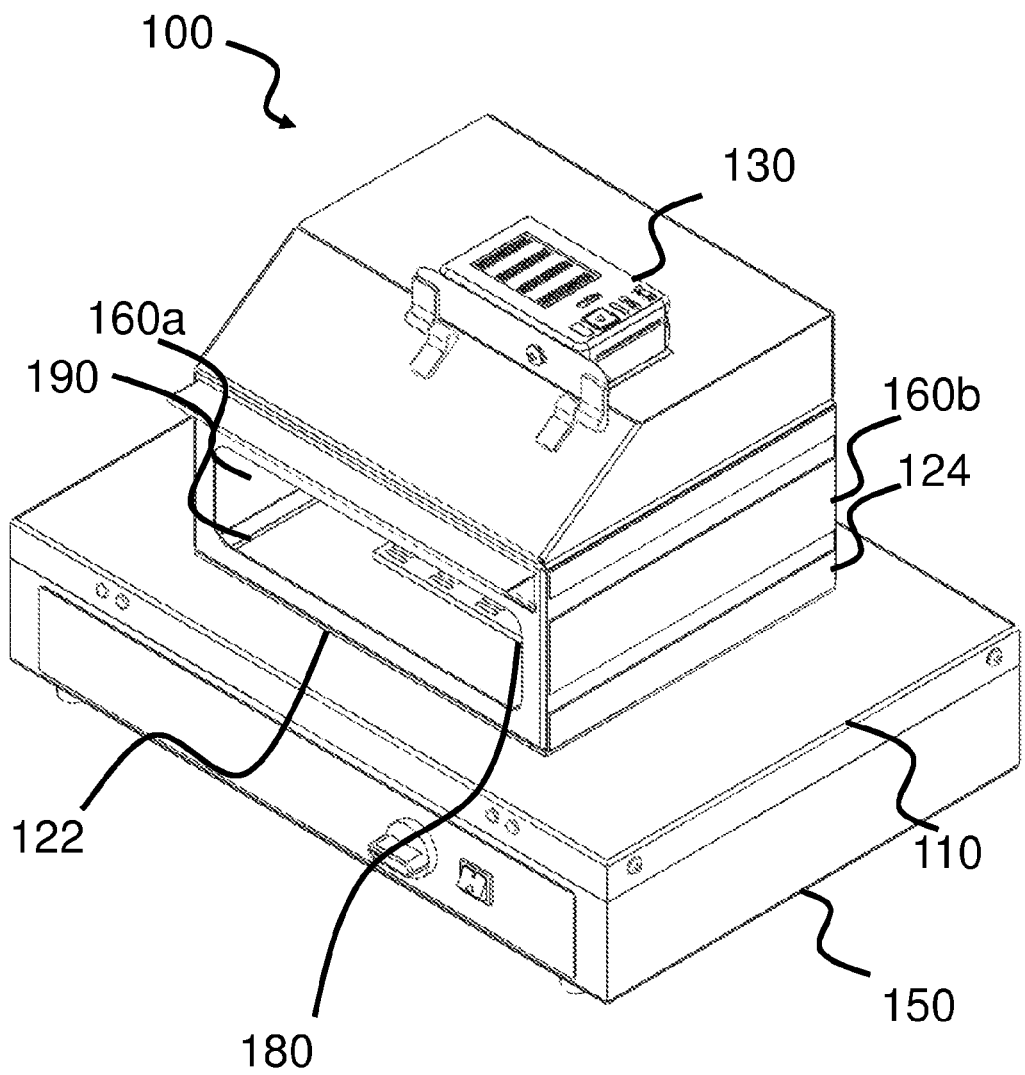
FIG. 7 shows the imaging apparatus of FIG. 6 with a transilluminator that has the platform energized, revealing optical contrast within the object, and the camera apparatus capturing an image of the object.

FIG. 7 shows imaging apparatus 100 of FIG. 6 with transilluminator 150 energized, revealing optical contrast within enclosed object 180, and camera apparatus 130 capturing and displaying an image of enclosed object 180. The optical contrast may exhibit absorption variation within the enclosed object. Alternately, the optical contrast may include fluorescence variation within or on a surface the enclosed object. An excitation filter may be placed between the illumination source and enclosed object 180 to achieve high-sensitivity fluorescence detection. Also a fluorescence filter may be placed between enclosed object 180 and the camera to achieve high-sensitivity fluorescence detection. One of ordinary skill in the art can appreciate that in an alternative embodiment where a light source is positioned to illuminate the enclosed object from the same side as the imaging device that the optical contrast may include reflectance variation on a surface of enclosed object 180. One of ordinary skill in the art can appreciate that in an alternative embodiment wherein no illumination source is present that the optical contrast may include a luminescence or phosphorescence variation within or on a surface of enclosed object 180. Also shown is that enclosed object 180 is viewable through front viewport 190 integral to enclosure chassis 122. Front viewport 190 may simply be an additional opening formed in enclosure chassis 122; or alternately comprise a window formed out of a transparent material, wherein the window may have an optical filter, for example an ultraviolet blocking filter or an amber filter.

Figure 8:
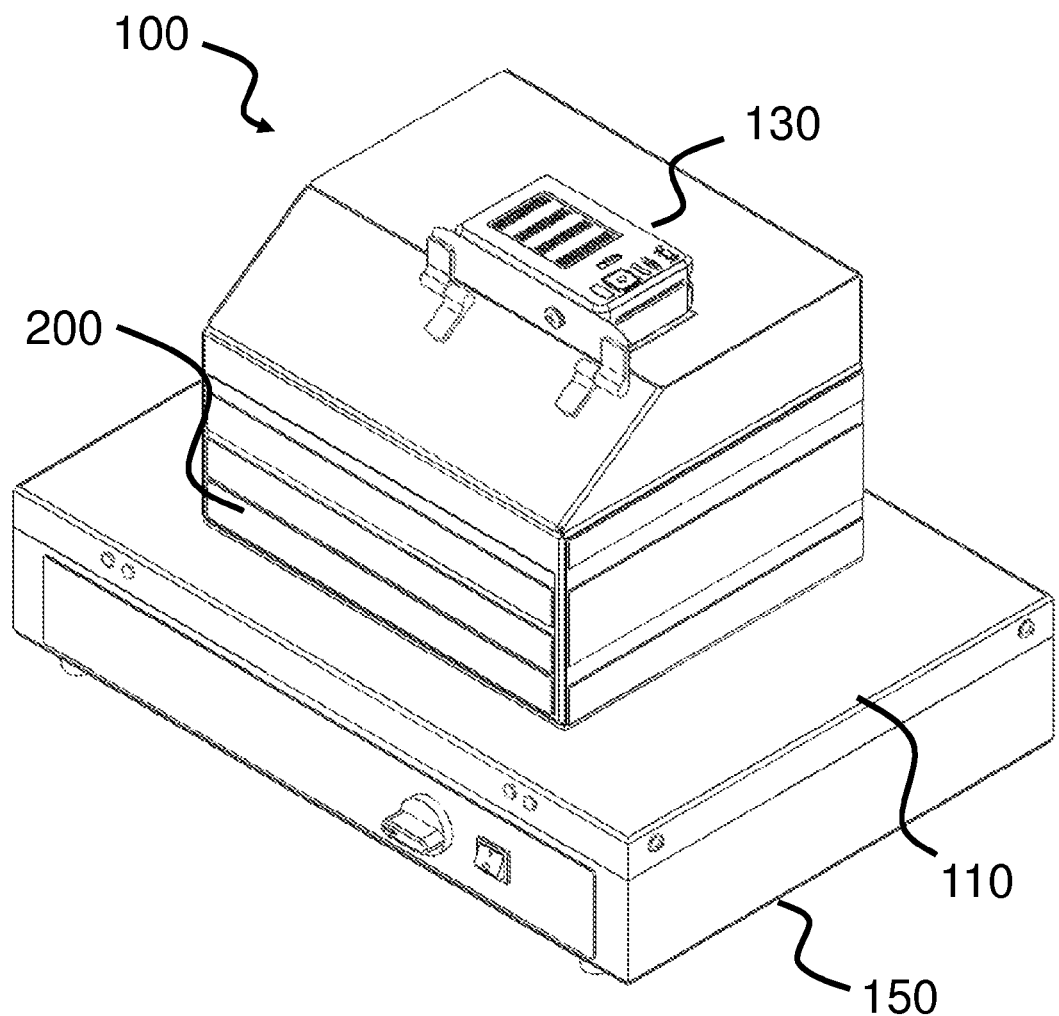
FIG. 8 shows the imaging apparatus of FIG. 7 with an additional foldable light-obstructing gasket deployed to cover a viewport of the enclosure chassis, and the imaging device capturing an image of the object.

FIG. 8 shows imaging apparatus 100 of FIG. 7 with second light-obstructing gasket 200 deployed in a closed position to cover front viewport 190, and camera apparatus 130 capturing and displaying an image of enclosed object 180. Covering viewport 190 may serve to increase the sensitivity or fidelity of the image of enclosed object 180. Second light-obstructing gasket 200 may be formed from a compressible material, such as polyurethane foam. Second foldable light-obstructing gasket 200 has a foldable front viewport access leaf. The foldable front viewport access leaf shown is comprised of magnetic panels attached, for example by an adhesive layer, to the compressible material of second light-obstructing gasket 200. In the closed position, the magnetic panels are on the side of second light-obstructing gasket 200 opposite enclosure chassis 122 and hence attracted to enclosure chassis 122 through second light-obstructing gasket 200. A compressing force is applied by the magnetic panels to compress second light-obstructing gasket 200 to enclosure chassis 122, to reinforce the integrity of second light-obstructing gasket 200 against light. One of ordinary skill in the art can appreciate that alternately the enclosure chassis may be formed from magnetic material and the foldable front viewport access leaf may have ferromagnetic panels and achieve the same function. The magnetic or ferromagnetic panels attached to the foldable front viewport access leaf may further serve to stiffen segments of the foldable front viewport access leaf.

Figure 9:
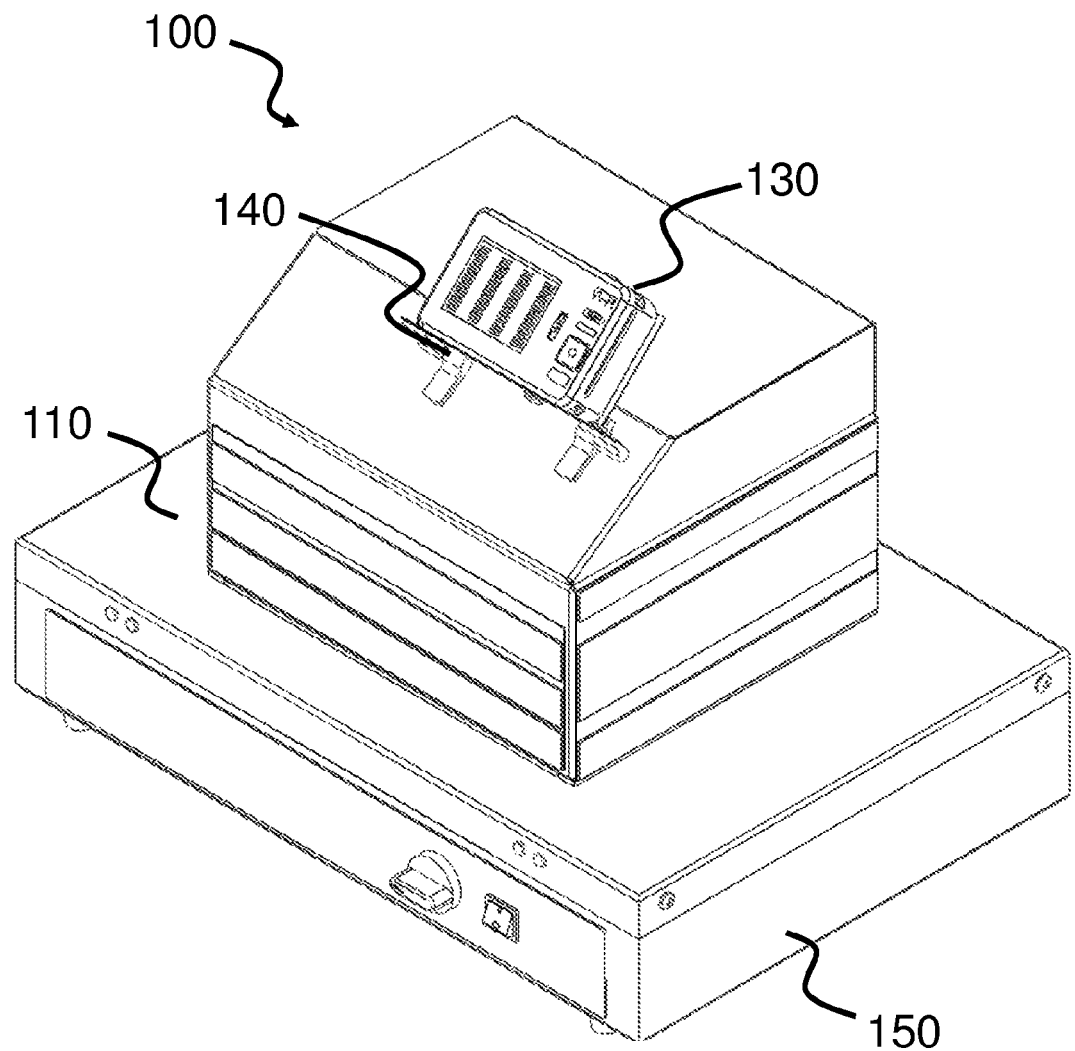
FIG. 9 shows the imaging apparatus of FIG. 8 with the camera apparatus in a second position, tilted away from the enclosure chassis, for viewing the image of the object.

FIG. 9 shows imaging apparatus 100 of FIG. 8 with camera apparatus 130 in a second position, tilted away from the imaging aperture (not shown in FIG. 9), for viewing a displayed image of enclosed object 180 on the integral display of camera apparatus 130.

Figure 10:
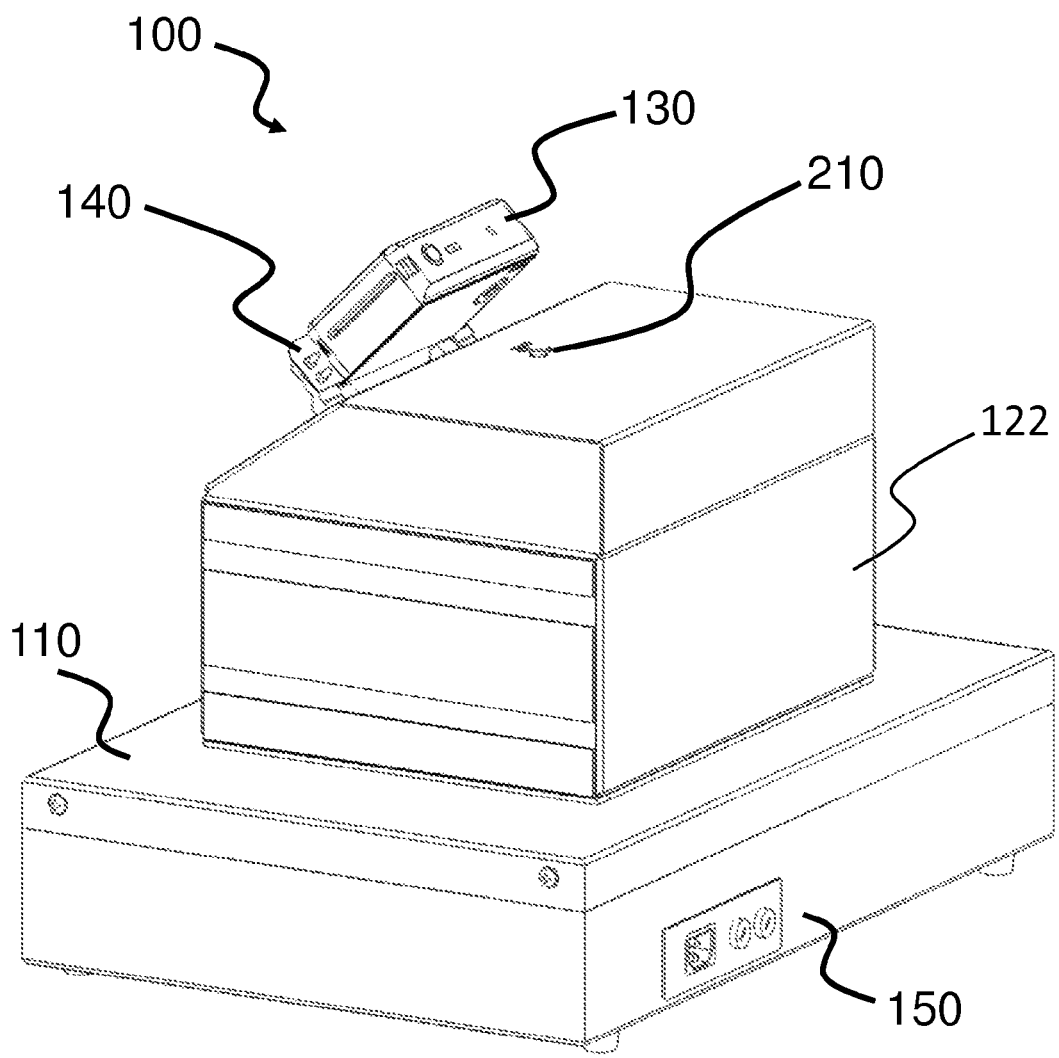
FIG. 10 shows the imaging apparatus of FIG. 9 viewed from a different perspective to show the opening formed in the enclosure chassis for exposing the object to the camera apparatus.

FIG. 10 shows imaging apparatus 100 of FIG. 9 viewed from a different perspective to illustrate an imaging aperture 210 formed in enclosure chassis 122 for exposing enclosed object 180 to camera apparatus 130. Fixture 140 has a pair of hinges that provide the ability to position camera apparatus 130 in a plurality of positions. One of ordinary skill in the art can appreciate that the fixture may alternately have one hinge to provide the same function. The plurality of positions includes a first position, as shown in FIGS. 1 to 8, wherein camera apparatus 130 is abutted against imaging aperture 210, for example for capturing at least one image of enclosed object 180. The plurality of positions further includes a second position, as shown in FIGS. 9 and 10, wherein camera apparatus 130 is tilted away from imaging aperture 210, for example for tilting to a viewing angle to view the at least one image of enclosed object 180 or for docking or undocking camera apparatus 130 from fixture 140. The plurality of tilt positions may further include additional positions not shown. The pair of hinges may comprise a pair of friction hinges for holding camera apparatus 130 in at least one of the positions, for example the second position.

Figure 11:
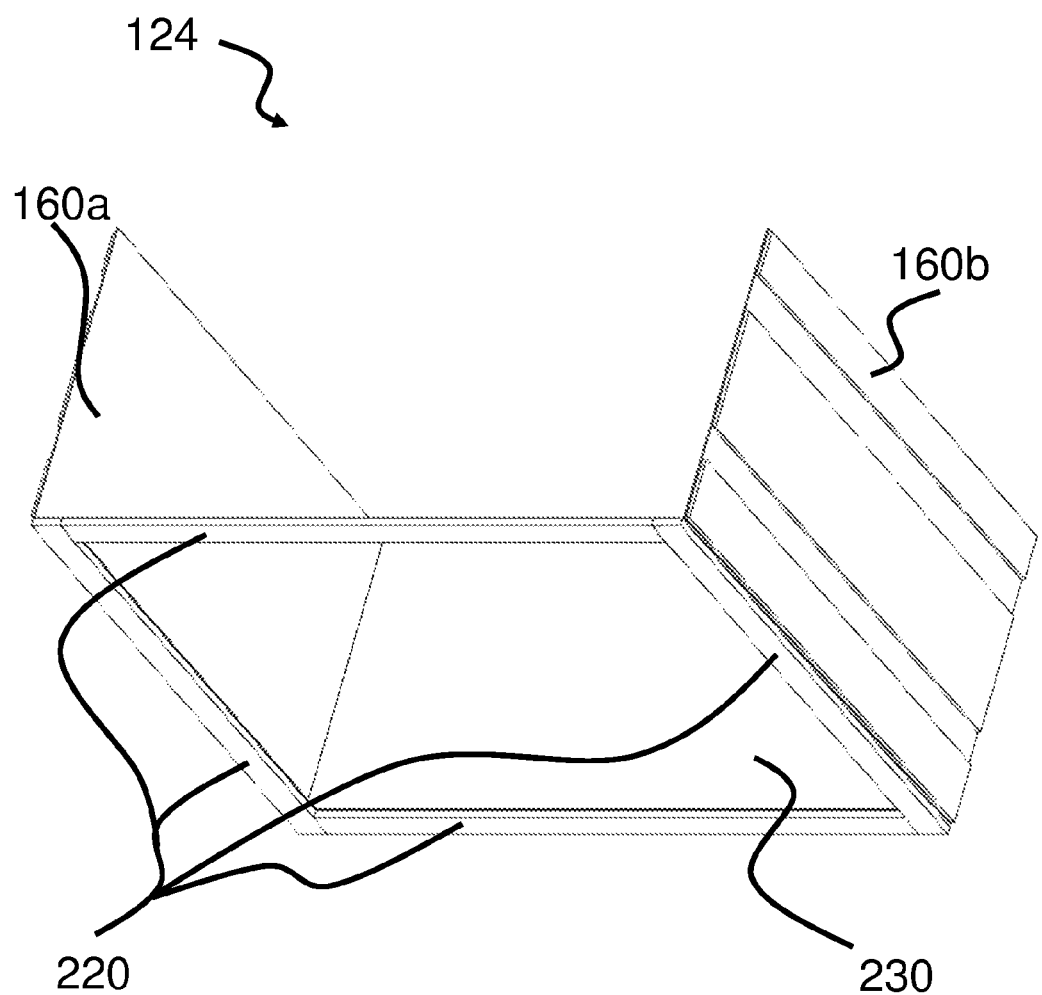
FIG. 11 shows a perspective view of the foldable light-obstructing gasket with the foldable lateral access leaves folded up.

FIG. 11 shows a perspective bottom view of first light-obstructing gasket 124 with foldable lateral access leaves 160a and 160b folded up. A set of magnets 220 provides magnetic attachment of first light-obstructing gasket 124 to platform 110; magnets in set 220 are attached to the bottom of first light-obstructing gasket 124. Also, a second opening, an illumination opening 230, formed for abutting enclosure 120 to platform 110, is shown.

Figure 12:
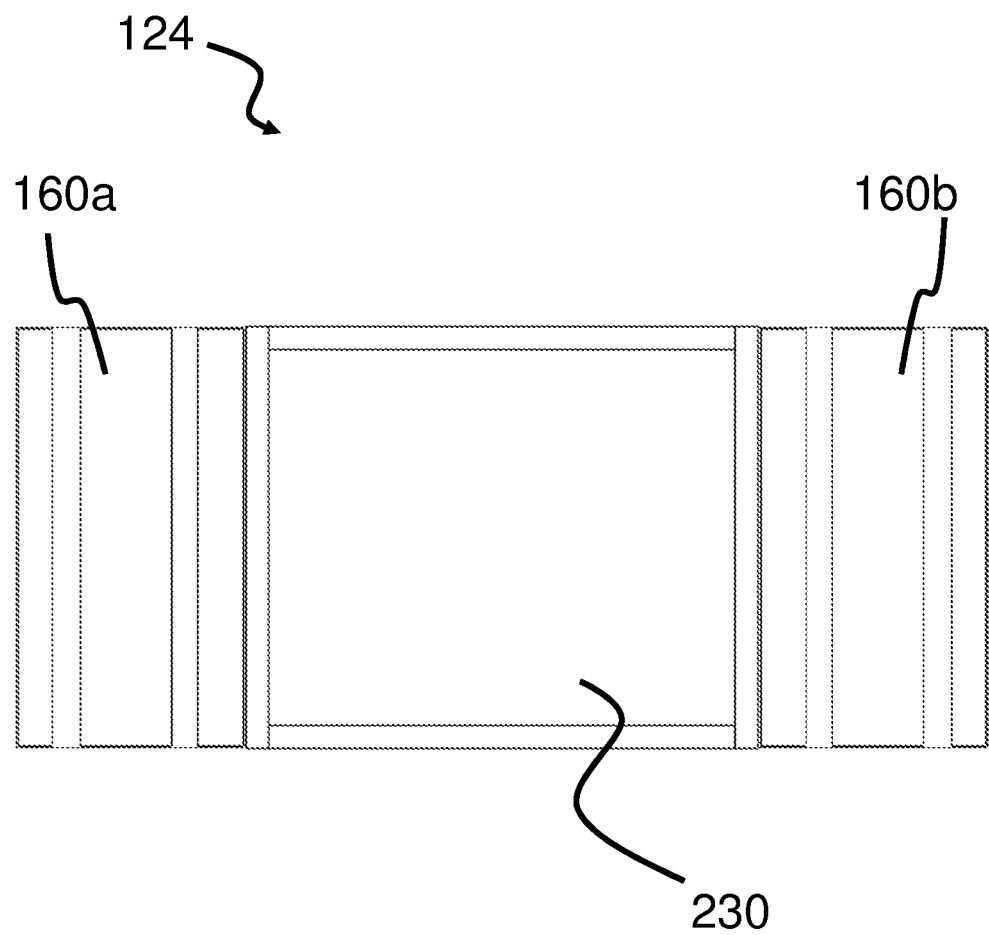
FIG. 12 shows a view of the light-obstructing gasket in a flattened configuration from below.

FIG. 12 shows a plan view of first light-obstructing gasket 124 in a flattened configuration, from below.

Figure 13:
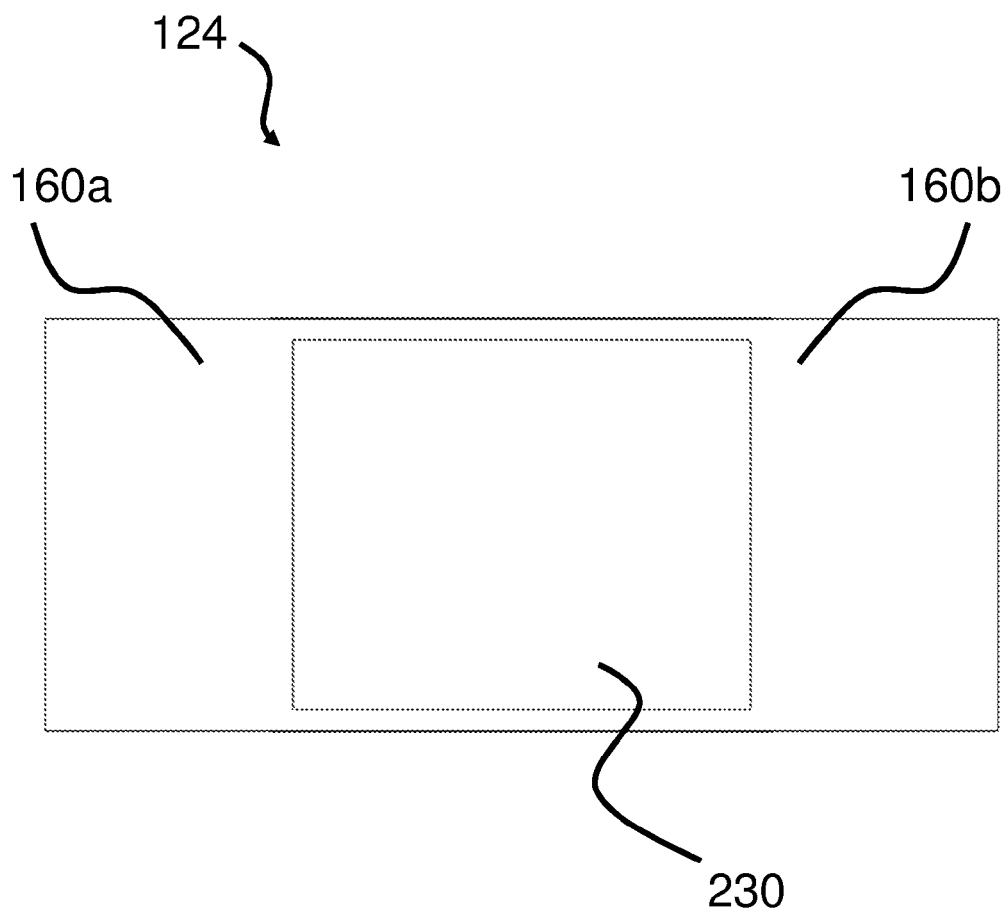
FIG. 13 shows a view of the light-obstructing gasket in a flattened configuration from above.

FIG. 13 shows a plan view of first light-obstructing gasket 124 in a flattened configuration from above, showing the face of first light-obstructing gasket 124 that generally interfaces with enclosure chassis 122, and more specifically wraps around the bottom and sides of enclosure chassis 122.

Figure 14:
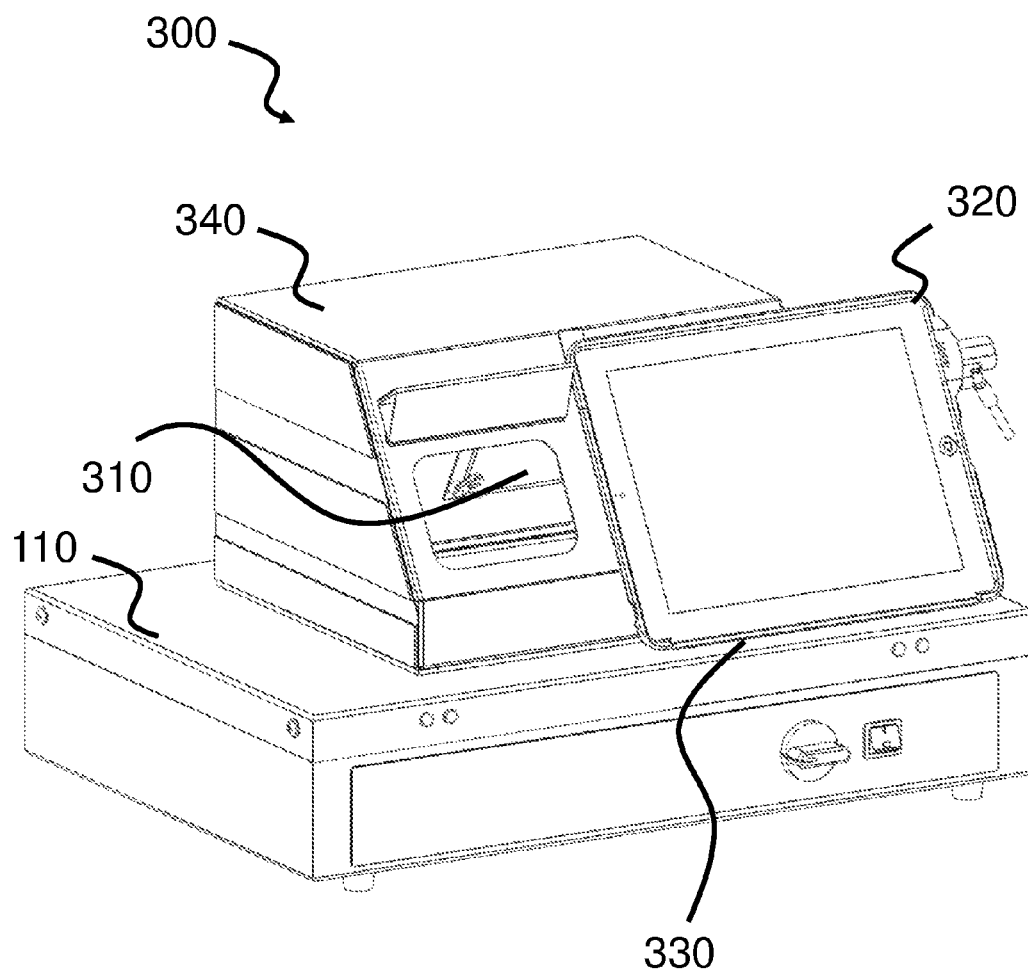
FIG. 14 shows a perspective view of another imaging apparatus, consistent with a second embodiment of the present invention, with the camera apparatus in a first position for abutting the camera apparatus to the opening formed in the enclosure chassis for exposing the at least one object to the camera apparatus.

FIG. 14 shows a perspective view of another imaging apparatus 300 consistent with an alternate embodiment of the present invention. Imaging apparatus 300 has all the features of imaging apparatus 100 shown in FIGS. 1-10, with the addition of a mirror 310 and a fixture comprising a receiving member 320. Receiving member 320 is sized and shaped to conform to camera apparatus 330, shown to be integral to a tablet device in this embodiment. FIG. 14 shows camera apparatus 330 in a first position abutting an aperture (not shown in FIG. 14) formed in enclosure chassis 340. Receiving member 320 provides a case for the tablet device, such as a lockable security case. Mirror 310 is internal to enclosure chassis 340. Mirror 310 folds the imaging path of camera apparatus 330. Folding the imaging path provides an advantage in that camera apparatus 330 can be oriented at an angle with respect to platform 110 to achieve a compact configuration of imaging apparatus 300.

Figure 15:
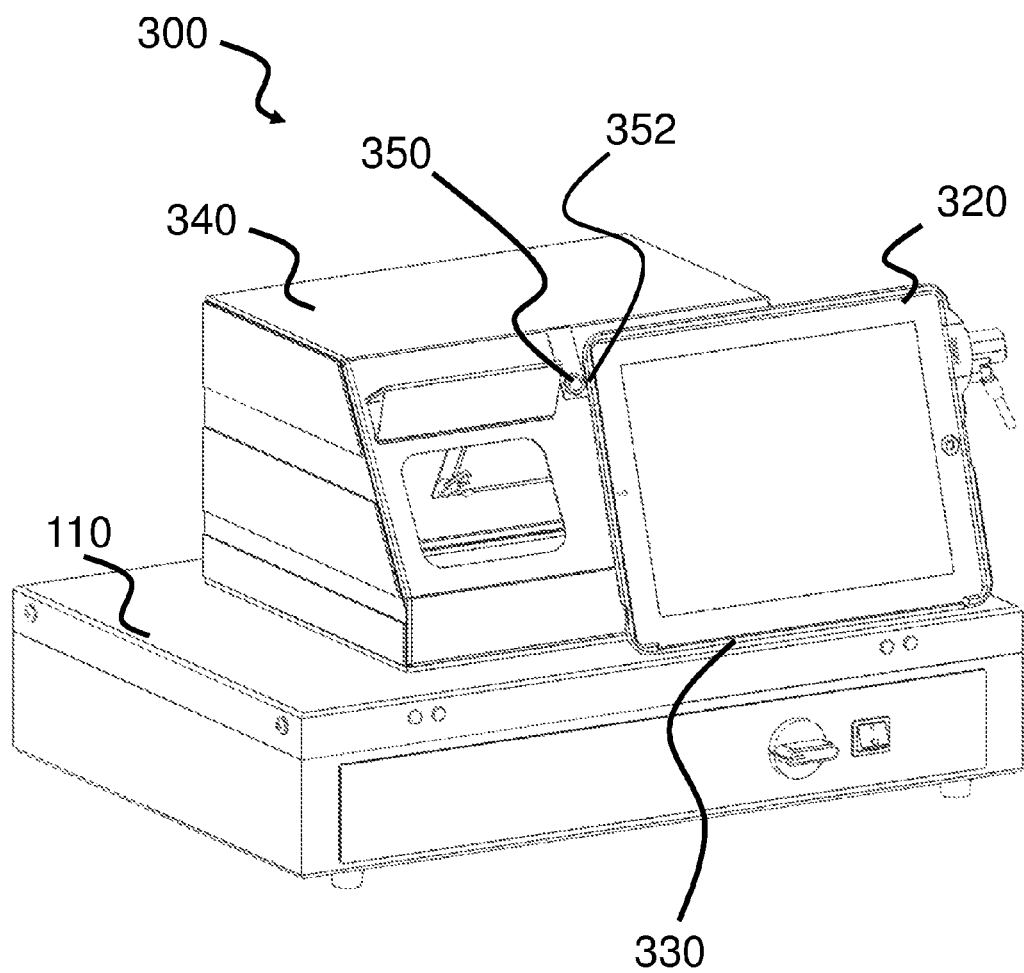
FIG. 15 shows the imaging apparatus of FIG. 14 with the camera apparatus in a second position away from the enclosure chassis.

FIG. 15 shows imaging apparatus 300 of FIG. 14 with camera apparatus 330 in a second position, tilted away from an imaging aperture 350, for unlocking the security case and removing camera apparatus 330 from imaging apparatus 300. Camera apparatus 330 is held in the second position by means of a pair of friction hinges of the fixture. In this embodiment imaging aperture 350 further has an optical filter 352.

Figure 16:
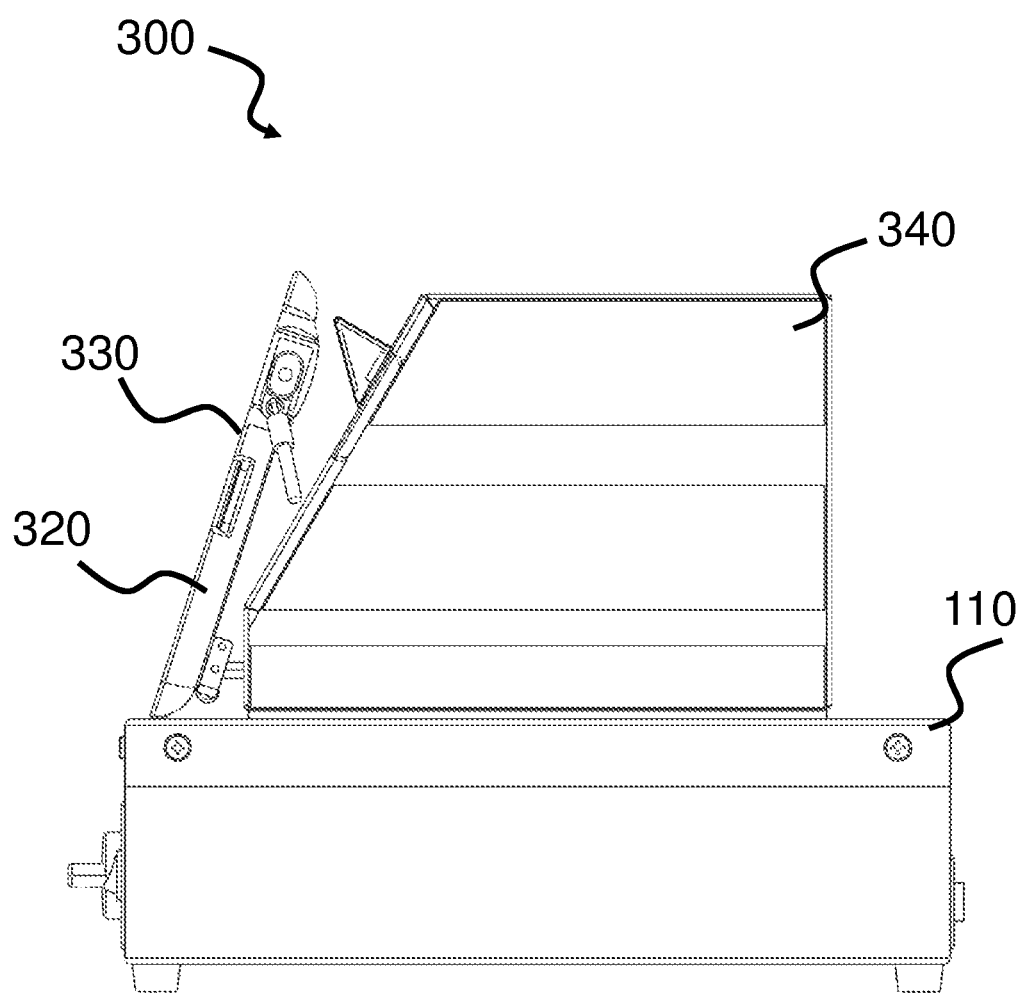
FIG. 16 shows a side view of the imaging apparatus of FIG. 15.

FIG. 16 shows a side view of imaging apparatus 300 of FIG. 15.

Figure 17:
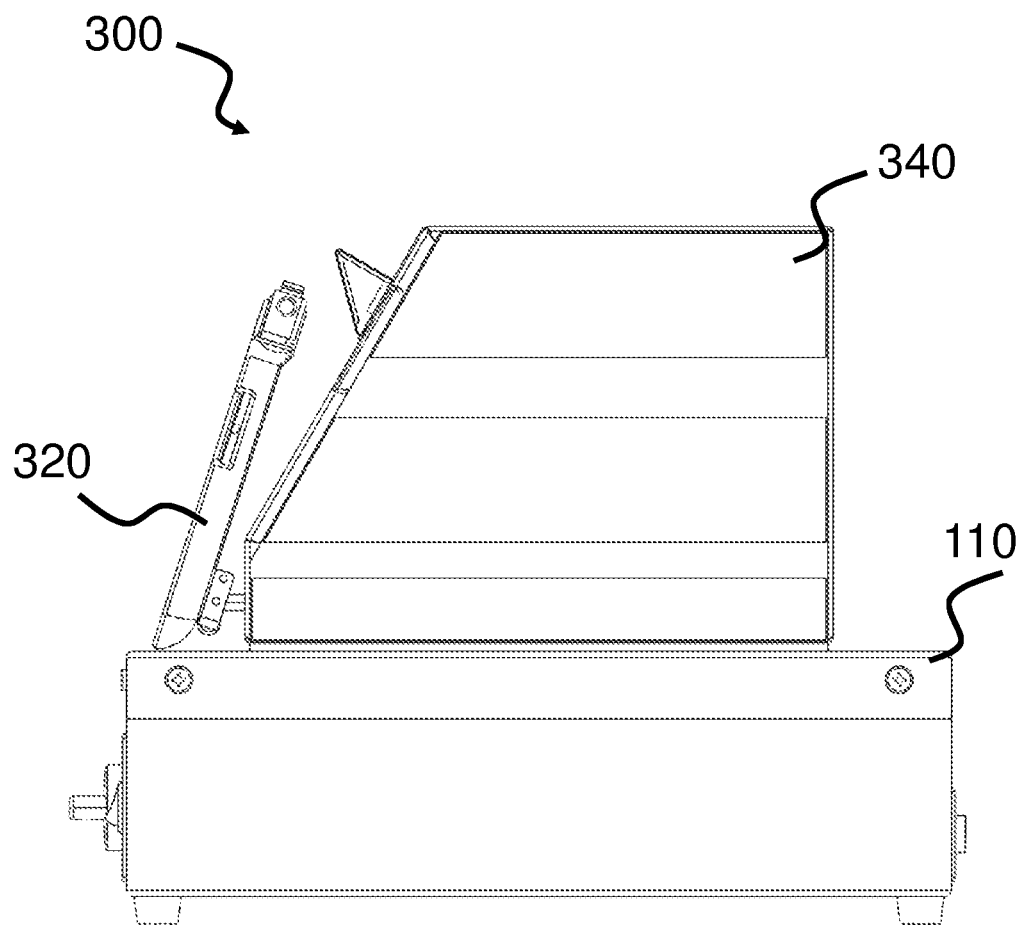
FIG. 17 shows the imaging apparatus of FIG. 16 with the camera apparatus removed from the imaging apparatus.

FIG. 17 shows imaging apparatus 300 of FIG. 16 with camera apparatus 330 removed from imaging apparatus 300.

Figure 18:
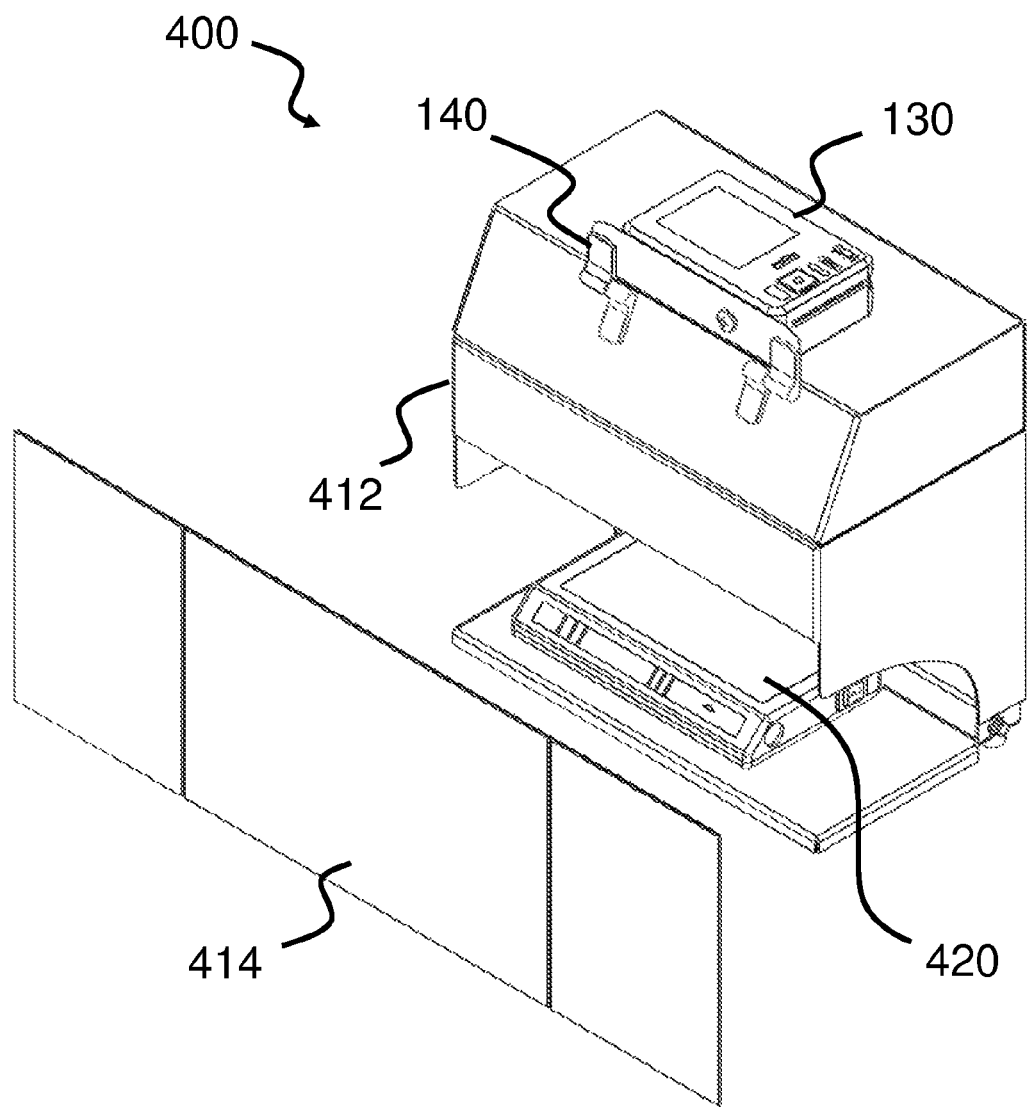
FIG. 18 shows an exploded perspective view of yet another imaging apparatus, consistent with a third embodiment of the present invention.

FIG. 18 shows an exploded perspective view of an imaging apparatus 400, consistent with another alternate embodiment of the present invention, comprising an enclosure chassis 412 and a light-obstructing gasket 414; a platform 420 interior to enclosure chassis 412; and camera apparatus 130 mounted upon enclosure chassis 412 by means of fixture 140. Light-obstructing gasket 414 may be formed from a compressible material, such as polyurethane foam. Light-obstructing gasket 414 is shown in a flattened state.

Figure 19:
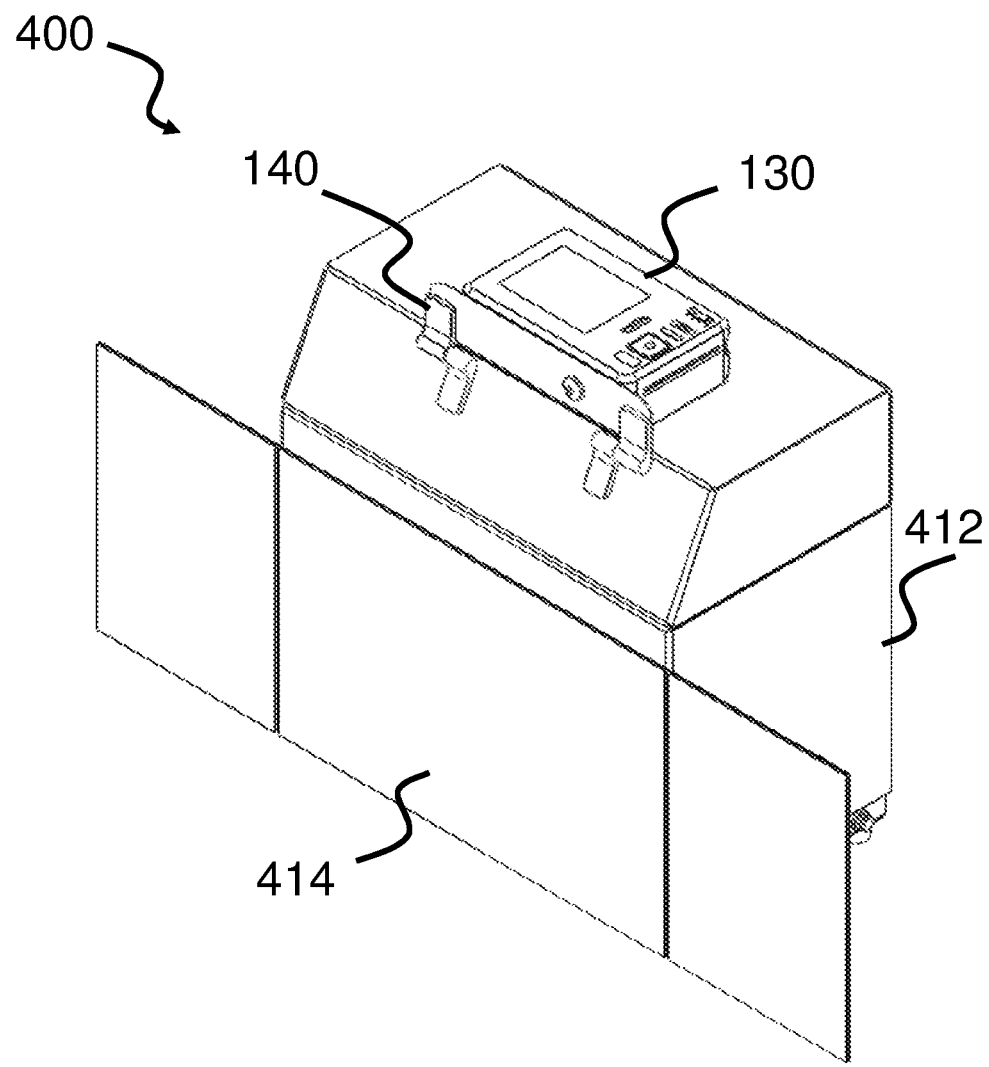
FIG. 19 shows a perspective view of the imaging apparatus of FIG. 18 in a partially assembled state.

FIG. 19 shows a perspective view of imaging apparatus 400 of FIG. 18 in a partially assembled state.

Figure 20:
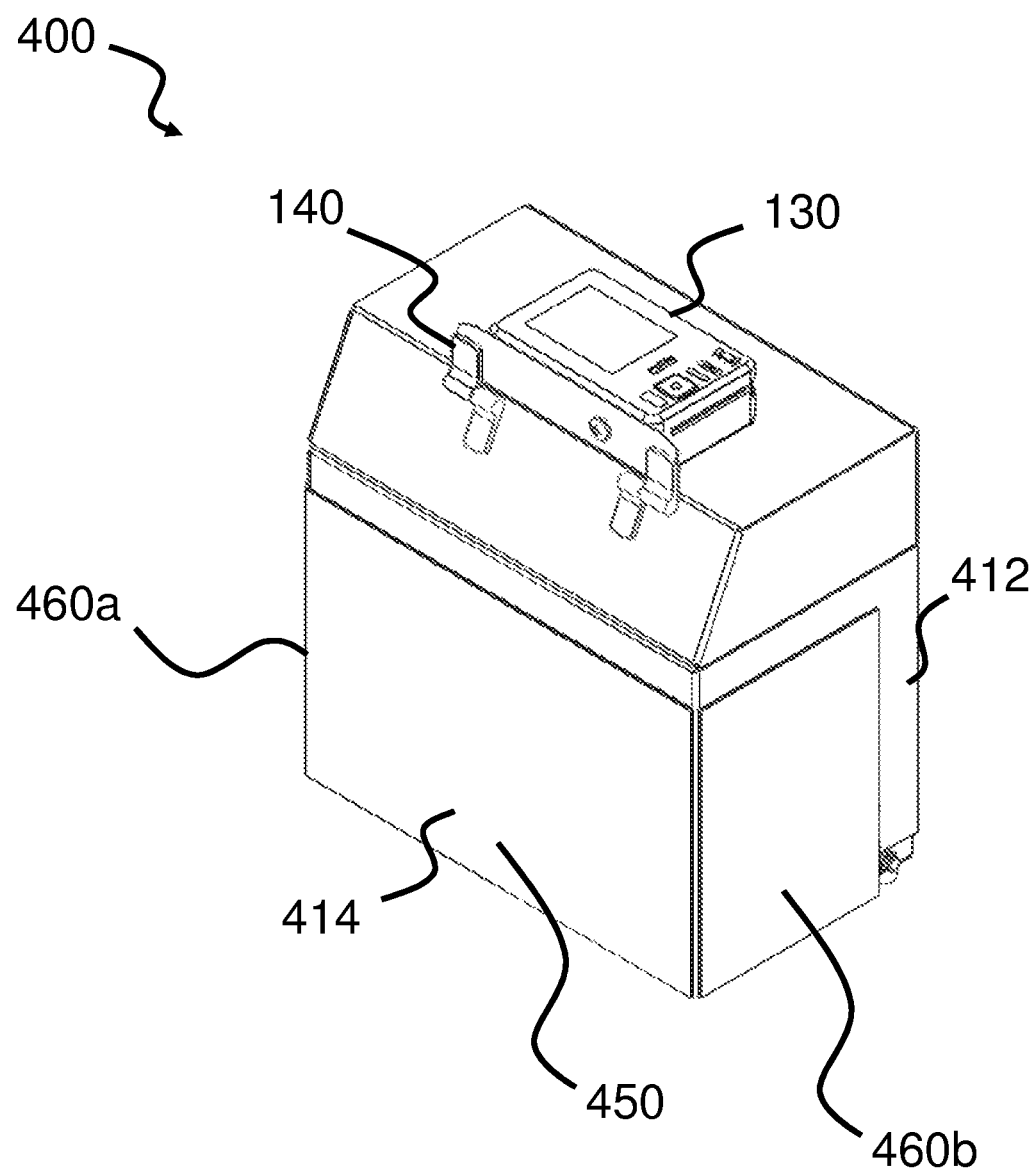
FIG. 20 shows a perspective view of the imaging apparatus of FIG. 19 in a fully assembled state.

FIG. 20 shows a perspective view of imaging apparatus 400 of FIG. 19 in a fully assembled state. Platform 420 provides support for the at least one enclosed object. Light-obstructing gasket 414 has a central front mounting panel 450 and two bilaterally opposed integral foldable lateral access leaves 460a and 460b shown in a closed position for complementing the opacity of imaging apparatus 400 in conjunction with enclosure chassis 412. One of ordinary skill in the art can appreciate that the light-obstructing gasket may alternately comprise a single integral movable lateral access leaf. Enclosure chassis 412 is formed from ferromagnetic material, such as steel, and both the central front mounting panel 450 and the foldable lateral access leaves 460a and 460b have magnetic panels attached, for example by an adhesive layer, to the compressible material of light-obstructing gasket 414. In the closed position, the magnetic panels are on the opposite side of light-obstructing gasket 414 as enclosure chassis 412 and hence magnetically attracted to enclosure chassis 412 through light-obstructing gasket 414. A compressing force is applied by the magnetic panels to compress light-obstructing gasket 414 to enclosure chassis 412 to both support light-obstructing gasket 414 and to reinforce the integrity of light-obstructing gasket 414 against light. One of ordinary skill in the art can appreciate that alternately the enclosure chassis may be formed from magnetic material and both the central front mounting panel and the foldable lateral access leaves may each have ferromagnetic panels and achieve the same function. The magnetic or ferromagnetic panels attached to both the central front mounting panel and the foldable lateral access leaves may further serve to stiffen the central front mounting panel and the foldable lateral access leaves.

Figure 21:
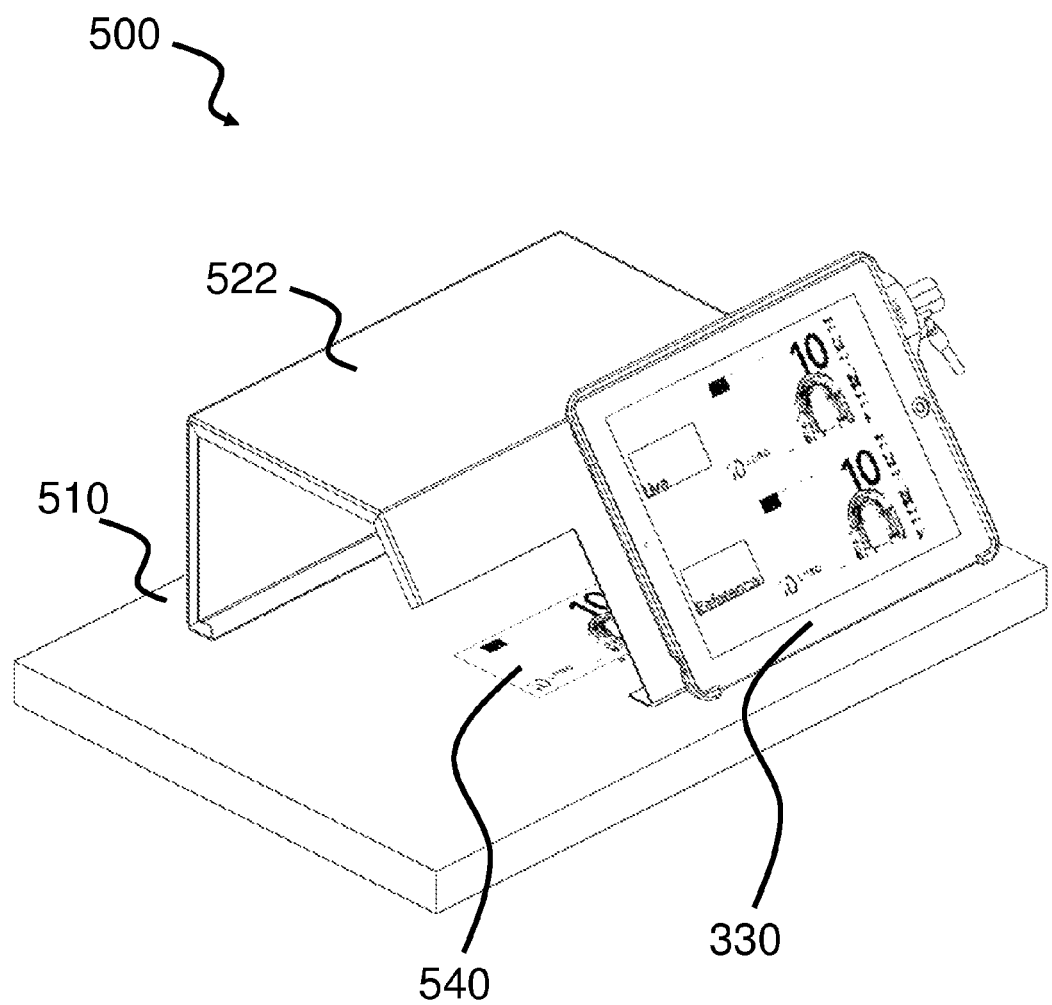
FIGS. 21-29 show yet another imaging apparatus, consistent with a fourth embodiment of the present invention, for counterfeit article detection.

FIG. 21 shows a perspective view of yet another imaging apparatus 500, consistent with an alternate embodiment of the present invention, related to counterfeit article detection, comprising: platform 510; enclosure chassis 522; and camera apparatus 330, mounted upon the enclosure by means of a fixture. Enclosure chassis 522 is formed to partially encompass a volume capable of containing at least one enclosed object and platform 510 is for providing support for the at least one enclosed object. Platform 510 further provides support for enclosure chassis 522 having an opening formed for abutting enclosure chassis 522 to platform 510. Enclosed object 540 is shown placed atop platform 510 and positioned within a field of view of the camera integral to camera apparatus 330. In the example shown, enclosed object 540 is a banknote. Other examples of objects relevant to counterfeit article detection include but are not limited to driver's licenses, passports, credit cards, bank checks, casino tokens, and pill bottles. The examples of objects relevant to counterfeit article detection may be both a reproduced artwork printed using ink visible by means of reflectance imaging under visible illumination such as white light, and either the presence, as often the case for authentic articles, or absence, as often the case for counterfeit articles, of a fluorescent authentication substance, such as fluorescent artwork or a fluorescent strip, visible by means of fluorescence imaging when excited by ultraviolet illumination. One of ordinary skill in the art can appreciate that certain types of illumination, for example blue light illumination or near-infrared illumination, may also serve as excitation light for fluorescence imaging.

Figure 22:
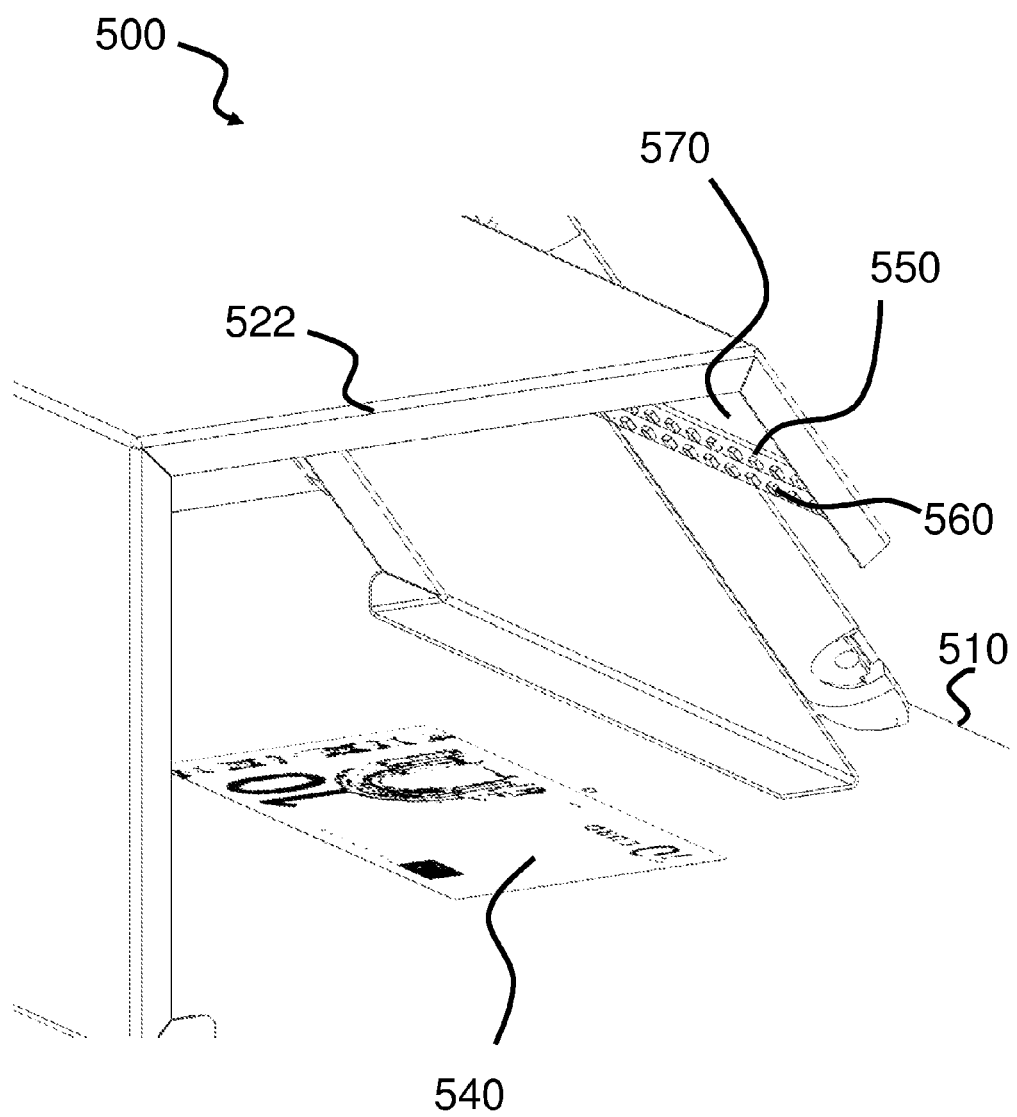

FIG. 22 shows a perspective interior view of imaging apparatus 500 of FIG. 21. Visible light source 550 is shown as a strip of white light emitting diodes (LEDs) with wavelength profiles for visible light emission, and ultraviolet light source 560, shown as a strip of ultraviolet light emitting diodes having wavelength profiles for ultraviolet (UV) light emission. The visible and UV wavelength profiles are considered to be substantially non-overlapping, with less than 20% of their emitted light energy at shared wavelengths. The LEDs are positioned on an interior surface 570 of enclosure chassis 522 as illumination sources for illuminating the field of view of the camera integral to camera apparatus 330. One of ordinary skill in the art can appreciate that alternative visible and ultraviolet illumination sources, for example cold cathode fluorescent lamps, can be used to serve the same function. In FIGS. 21-24, visible light source 550 is energized and ultraviolet light source 560 is not energized, so that the reproduced artwork printed using ink that is visible under visible illumination can be imaged by means of reflectance imaging.

Figure 23:
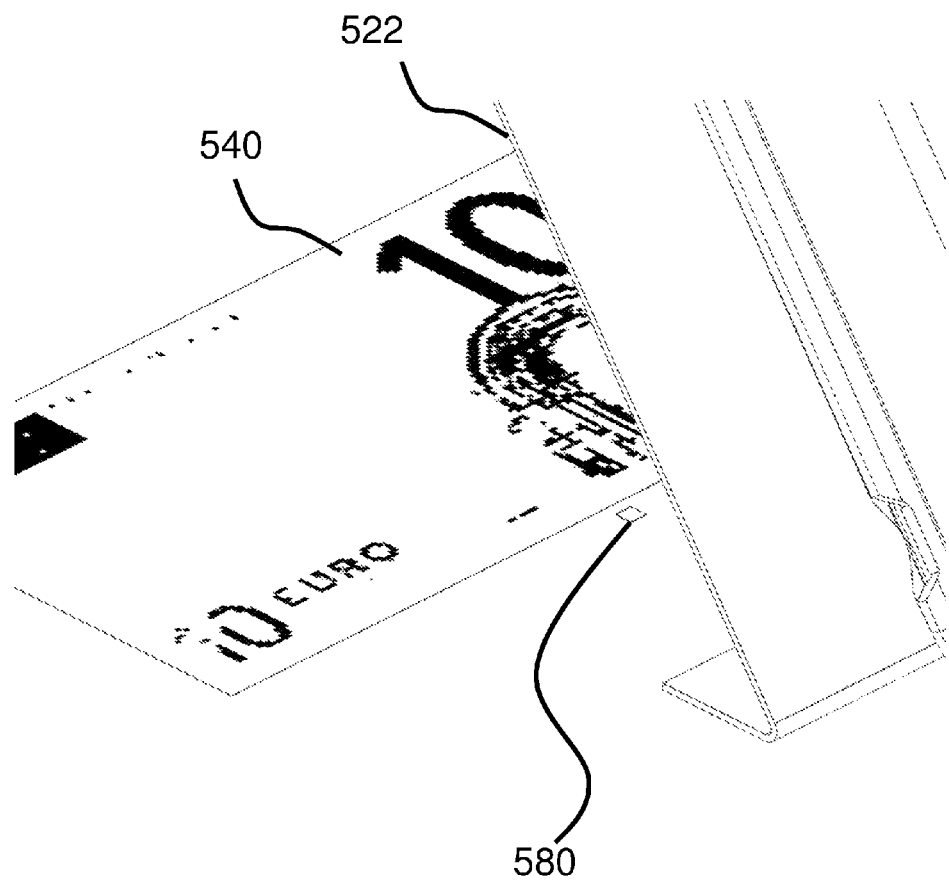

FIG. 23 shows a close-up view of a portion of imaging apparatus 500 of FIG. 21, including an illumination status indicator 580. Illumination status indicator 580 is for differentiating between two illumination sources having different wavelength profiles. Illumination status indicator 580 may be formed using a fluorescent substance, such as a fluorescent dye or fluorescent inorganic nanoparticles, for example. Illumination status indicator 580 may further include a swatch of material wherein the fluorescent substance is coated onto, printed onto, or incorporated into the swatch of material. Platform 510 may comprise a transparent or translucent substrate and illumination status indicator 580 may be reverse printed onto an underside of the substrate, for example, using fluorescent ink Illumination status indicator 580 lies within the field of view of camera apparatus 330 at the imaging aperture. Illumination status indicator 580 indicates the type of illumination it receives. According to an embodiment of the present invention, illumination status indicator 580 verifies that ultraviolet (UV) light source 560 is energized, but is not indicative of an energized state of visible light source 550 because the fluorescent substance of illumination status indicator 580 is either only weakly excited or not excited at all for light at UV wavelengths and therefore does not emit substantial fluorescence with only visible light illumination. In FIG. 23, illumination indicator 580 presents an appearance, for example a dim appearance, to camera apparatus 330 indicating that the incident illumination is not light from ultraviolet light source 560, and therefore is light from visible light source 550.

Figure 24:
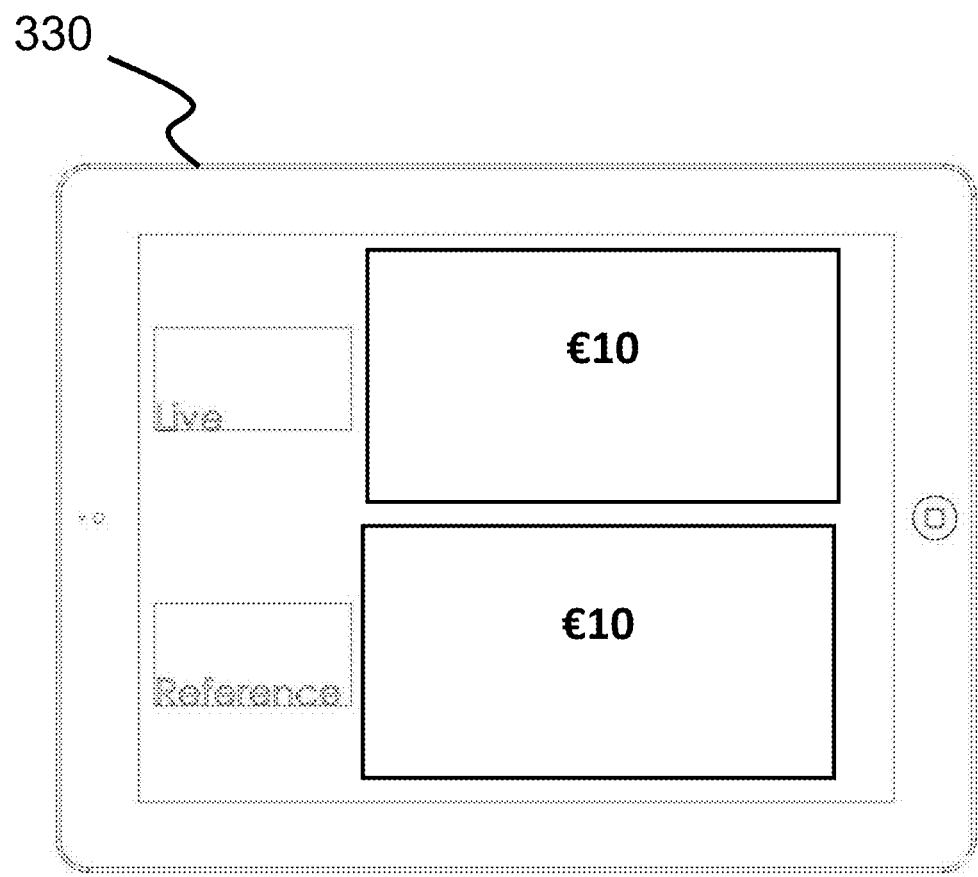

FIG. 24 shows camera apparatus 330 of FIG. 21, wherein the integral display of camera apparatus 330 displays the actual reflectance image of the enclosed object under visible illumination on the top half of the display and a retrieved reference reflectance image of a known authentic example of the enclosed object under visible illumination on the bottom half of the display. The retrieved reference reflectance image may have been retrieved from an archive manually by an operator, not shown, of imaging apparatus 500 by means known to those of ordinary skill in the art, such as a bookmark for a uniform resource locator (URL), an internet search, or browsing of an electronic photo album. Alternately, the retrieved reference reflectance image may have been retrieved automatically, for example by an image processor, not shown, integral to camera apparatus 330, executing image recognition code for recognizing the current reflectance image. The image processor may further interpret the image of illumination indicator 580 to determine that the image was acquired using visible illumination, using prior knowledge of the image coordinates of illumination indicator 580 and the expected image data corresponding to illumination indicator 580, for example whether the image of illumination indicator 580 is dimmer than a predetermined threshold. The image processor may then use the result of the interpretation of illumination indicator 580 to guide the retrieval of the reference reflectance image. Preferably illumination indicator 580 is positioned on platform 510 such that it appears near an edge of the field of view of the camera to maximize the fraction of the field of view available for enclosed object 540. FIG. 24 shows that the current reflectance image and the retrieved reference reflectance image match.

Figure 25:
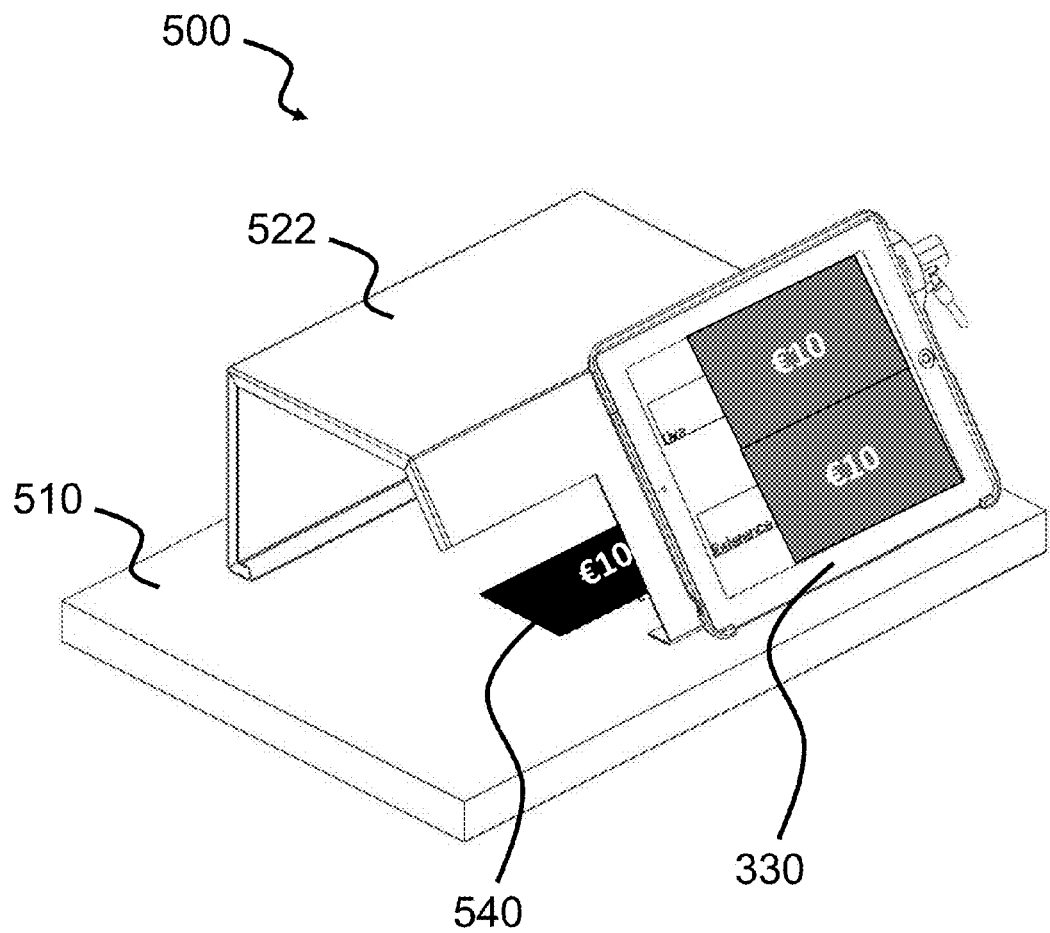
Figure 26:
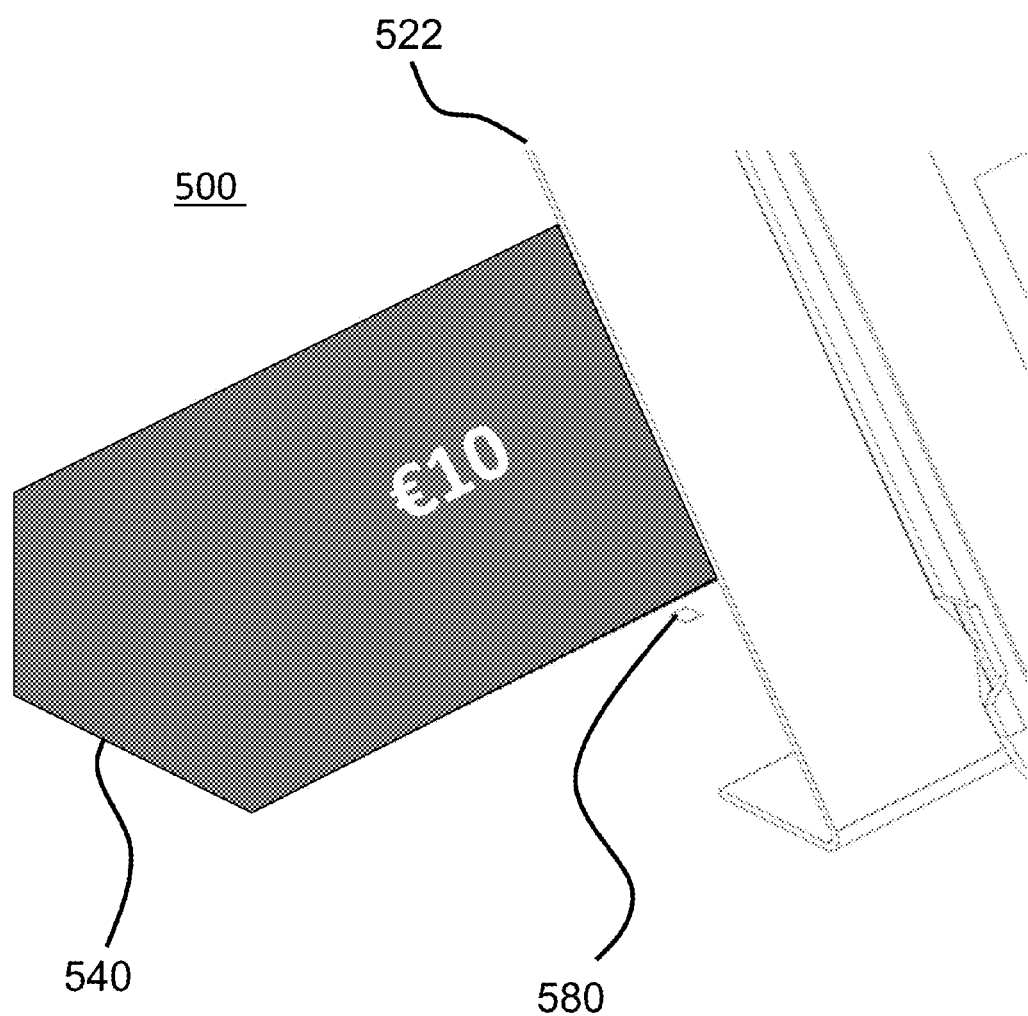
Figure 27:
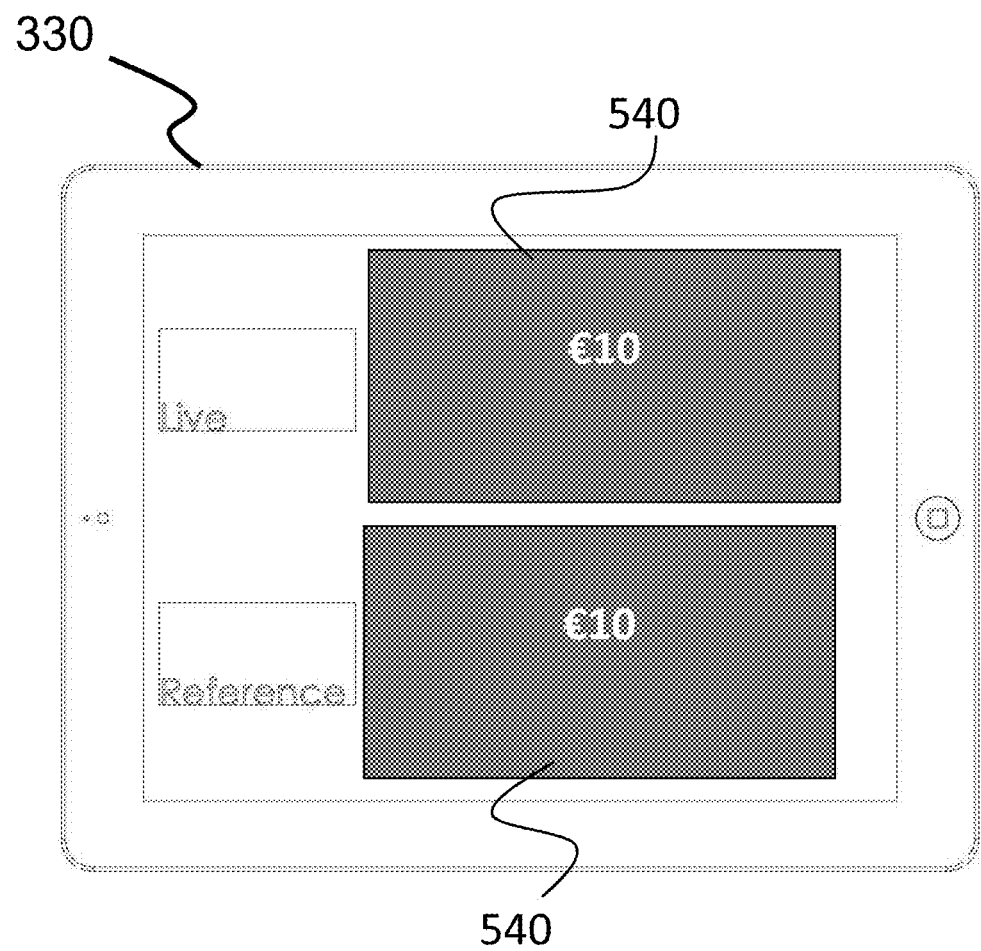

FIG. 25 shows another perspective view of imaging apparatus 500 of FIG. 21. In FIGS. 25-27, ultraviolet light source 560 of FIG. 22 is energized and visible light source 550 is de-energized, so that the fluorescent authentication substance, if present, may be imaged by means of fluorescence imaging. In FIGS. 25-27, enclosed object 540 is authentic and comprises the fluorescent authentication substance.

FIG. 26 shows a close-up view of imaging apparatus 500 of FIG. 25. Illumination status indicator 580 is indicative of an energized state of ultraviolet light source 560 because the fluorescent substance of illumination indicator 580 is strongly excited with incident light at UV wavelengths and therefore emits substantial fluorescence. In FIG. 26 illumination indicator 580 presents an appearance, for example by a bright appearance, such that it is readily perceptible to camera apparatus 330, indicating that the incident illumination is ultraviolet light from ultraviolet light source 560, and therefore not light from visible light source 550.

FIG. 27 shows camera apparatus 330 of FIG. 25, wherein the integral display of camera apparatus 330 displays a fluorescence image of enclosed object 540 under ultraviolet illumination on the top half of the display and a retrieved reference fluorescence image of a known authentic example of enclosed object 540 under ultraviolet illumination on the bottom half of the display. The retrieved reference fluorescence image may have been retrieved from an archive manually by an operator, not shown, of imaging apparatus 500 by means known to those of ordinary skill in the art, such as a bookmark for a uniform resource locator (URL), an internet search, or browsing of an electronic photo album. Alternately, the retrieved reference fluorescence image may have been retrieved automatically, for example by an image processor, not shown, integral to camera apparatus 330, executing image recognition code for recognizing the current fluorescence image. The image processor may further interpret the image of illumination indicator 580 to determine that the image was acquired using ultraviolet illumination, using prior knowledge of the image coordinates of illumination indicator 580 and the expected image data corresponding to illumination indicator 580, for example whether the image of illumination indicator 580 is brighter than a predetermined threshold. The image processor may then use the result of the interpretation of illumination indicator 580 to guide the retrieval of the reference fluorescence image. FIG. 27 shows that the current fluorescence image and the retrieved reference fluorescence image match, since the fluorescent authentication substance appears present in both images. The side-by-side display of the current fluorescence image and the retrieved reference fluorescence image may be useful for an operator to determine the authenticity of enclosed object 540 based on its current fluorescence image.

Figure 28:
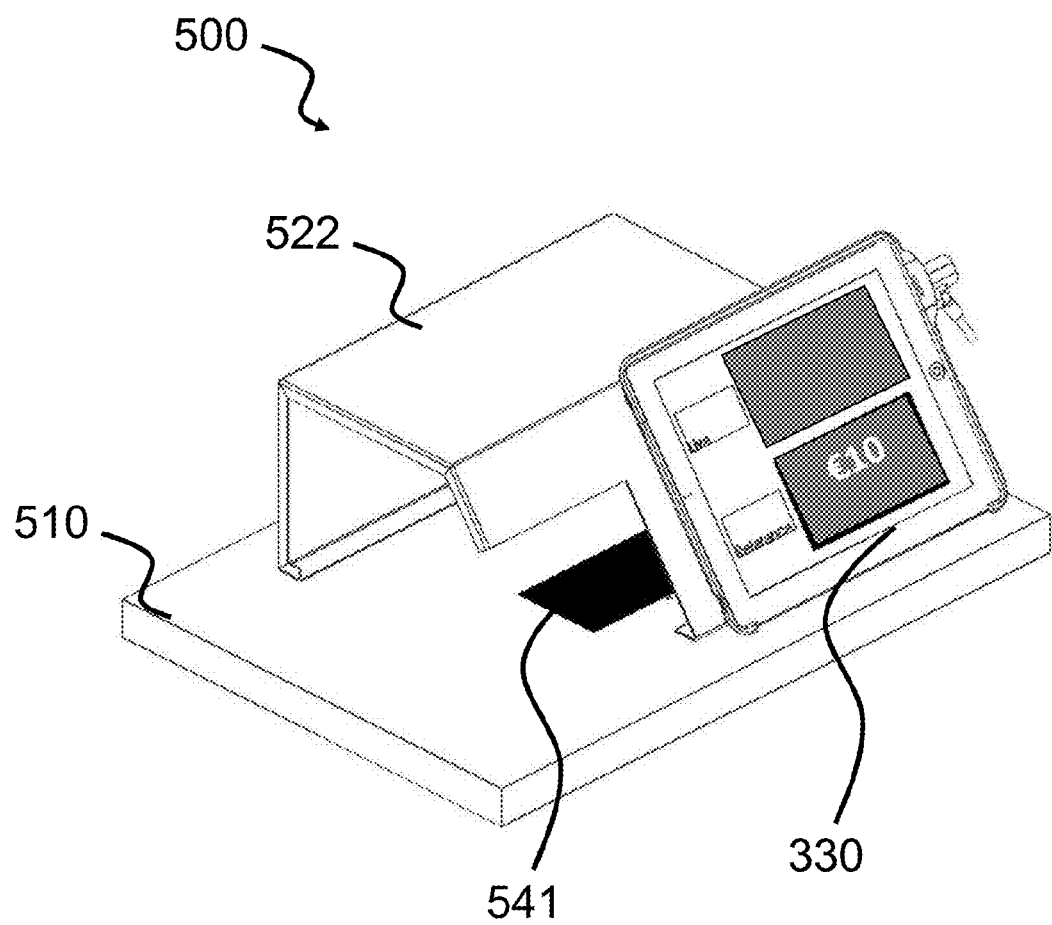
Figure 29:
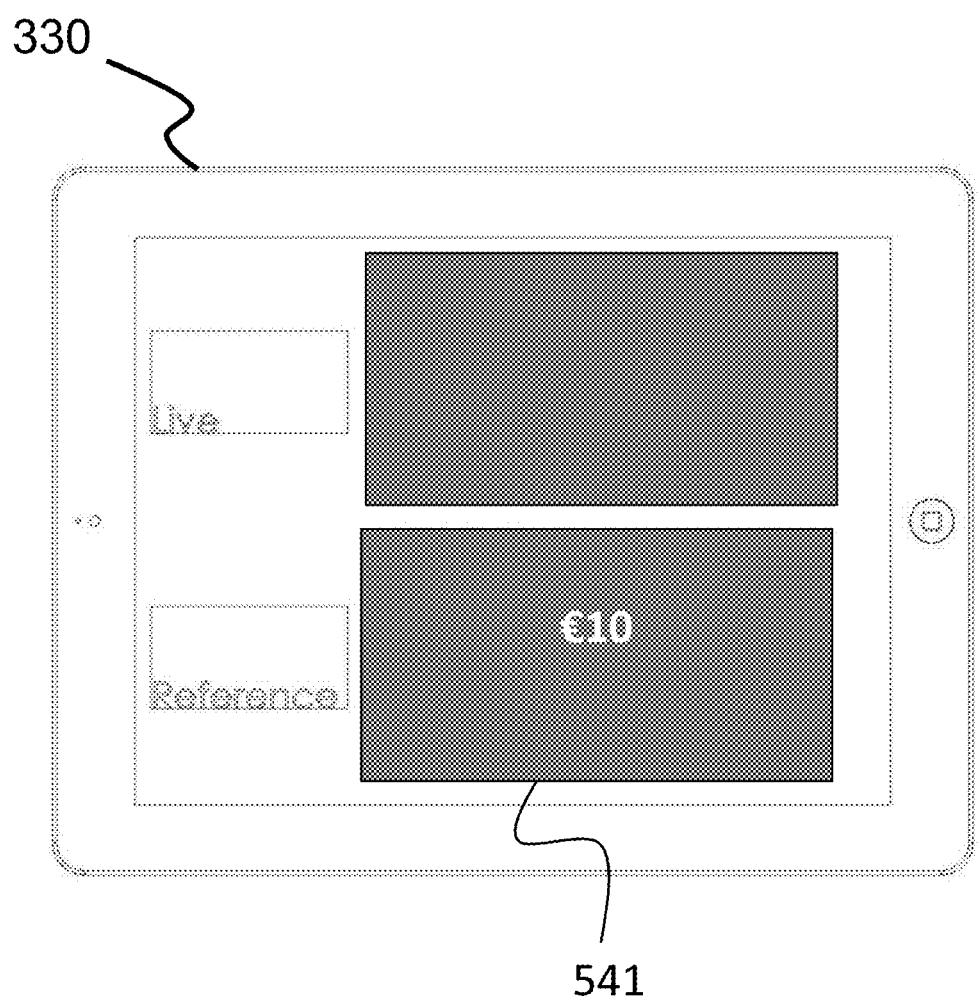

FIG. 28 shows another perspective view of imaging apparatus 500 of FIG. 21. In FIGS. 28-29, ultraviolet light source 560 of FIG. 22 is energized and visible light source 550 is not energized, so that the fluorescent authentication substance, if present, may be imaged by means of fluorescence imaging. In FIGS. 28-29, enclosed object 541 is counterfeit and does not include the fluorescent authentication substance.

FIG. 29 shows camera apparatus 330 of FIG. 28, wherein the integral display of camera apparatus 330 is displaying a current fluorescence image of the counterfeit enclosed object 541 under ultraviolet illumination on the top half of the display and a retrieved reference fluorescence image of a known authentic example of counterfeit enclosed object 541 under ultraviolet illumination on the bottom half of the display. FIG. 29 shows that the current fluorescence image and the retrieved reference fluorescence image do not match in that the fluorescent authentication substance appears present in the retrieved reference fluorescence image but not in the current fluorescence image. The side-by-side display of the current fluorescence image and the retrieved reference fluorescence image may be useful for an operator to make a determination of the lack of authenticity of the counterfeit enclosed object based on its current fluorescence image, whereas the current reflectance image of counterfeit enclosed object 541 may still match the retrieved reference reflectance image of a known authentic example of counterfeit enclosed object 541 and therefore be insufficient to judge the authenticity of counterfeit enclosed object 541.

Figure 30A:
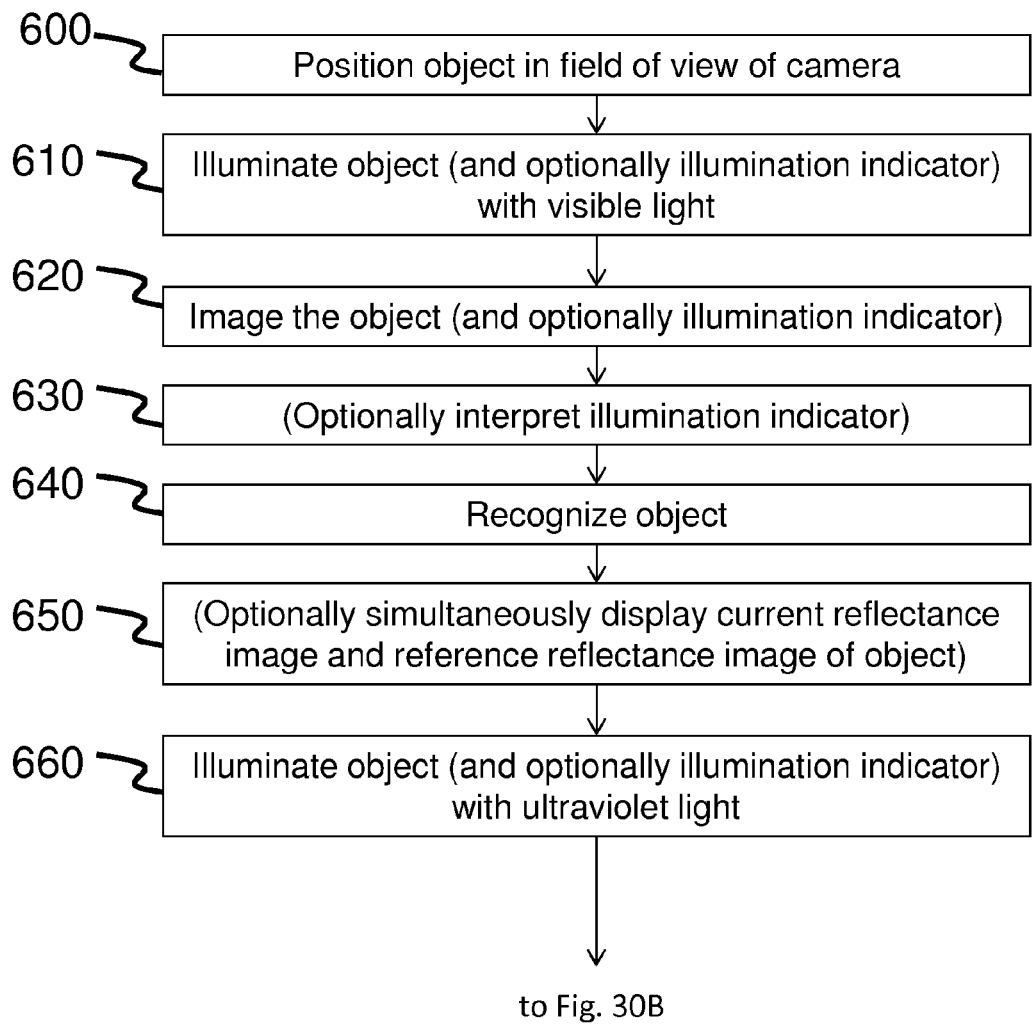
FIGS. 30A and 30B show a logic flow diagram of a method consistent with a fifth embodiment of the present invention related to using a counterfeit article detection apparatus adapted for mobile devices.
Figure 30B:
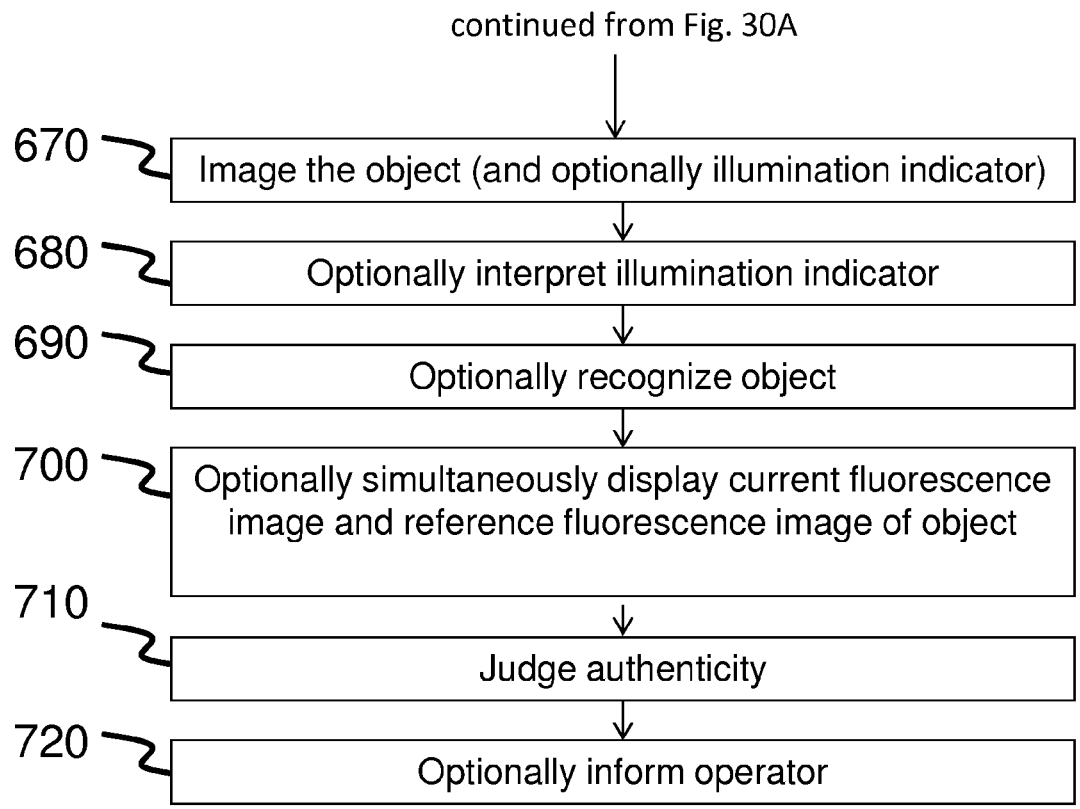

FIGS. 30A and 30B show a logic flow diagram of a method consistent with a fifth embodiment of the present invention related to using a counterfeit article detection apparatus adapted for mobile devices. The method has a series of steps. A first step 600 of the series of steps comprises positioning at least one object in a field of view of a camera integral to a mobile device. For example, the at least one object may be a banknote, driver's license, passport, credit card, bank check, casino token, or pill bottle, and can include both a reproduced artwork printed using ink visible under visible illumination such as white light, and either the presence or absence of a fluorescent authentication substance, such as fluorescent artwork or a fluorescent strip, visible by means of fluorescence under ultraviolet illumination. Optionally, at least one illumination indicator may also be positioned within the field of view of the camera alongside the at least one object. A second step 610 of the series of steps comprises illuminating the at least one object, and optionally the at least one illumination indicator, with visible illumination such as white light. A third step 620 of the series of steps comprises imaging the at least one object, and optionally the at least one illumination indicator, under visible illumination with the camera. An optional fourth step 630 of the series of steps comprises interpreting the illumination indicator to achieve an interpretation result corresponding to visible illumination, wherein the interpretation is automatically achieved by an image processor, for example integral to either the mobile device or a remote server. A fifth step 640 of the series of steps comprises recognizing the at least one object by means of image recognition, wherein the recognizing may be by the naked eye or alternately automatically achieved by the image processor by means of the interpretation result. An optional sixth step 650 of the series of steps comprises simultaneously displaying a current reflectance image of the at least one object and a reference reflectance image of the at least one object, wherein the reference image is retrieved from an archive by means of triggering a retrieval sequence based on the recognizing of the at least one object. A seventh step 660 of the series of steps comprises illuminating the at least one object, and optionally the at least one illumination indicator, with ultraviolet illumination to enable the at least one object, and optionally the at least one illumination indicator, to fluoresce, wherein the at least one object fluoresces if the fluorescent substance is present. An eighth step 670 of the series of steps comprises imaging the at least one object, and optionally the at least one illumination indicator, under the ultraviolet illumination with the camera. An optional ninth step 680 of the series of steps comprises interpreting the at least one illumination indicator to achieve an interpretation result corresponding to ultraviolet illumination, wherein the interpretation is automatically achieved by an image processor. An optional tenth step 690 of the series of steps comprises recognizing the at least one object by means of image recognition, wherein the recognizing may be by the naked eye or alternately automatically achieved by the image processor by means of the interpretation result. An optional eleventh step 700 of the series of steps comprises simultaneously displaying a current fluorescence image of the at least one object and a reference fluorescence image of the at least one object, wherein the reference image is retrieved from an archive by means of triggering a retrieval sequence based on the recognizing of the at least one object. A twelfth step 710 of the series of steps comprises judging the authenticity of the at least one object by comparing the current fluorescence image of the at least one object against the reference fluorescence image of the at least one object, wherein the judging may be by the naked eye or alternately automatically achieved by the image processor. An optional thirteenth step 720 of the series of steps comprises informing an operator of the counterfeit article detection apparatus regarding the authenticity, or lack thereof, of the at least one object, wherein the informing may be visible, audible, haptic, or any combination thereof.

While the present invention has been described in connection with various embodiments, many modifications will be readily apparent to those skilled in the art. Accordingly, embodiments of the invention are not limited to the above described embodiments and examples.

The invention has been described with reference to a number of embodiments; however, it can be appreciated that variations and modifications can be effected by a person of ordinary skill in the art without departing from the scope of the invention.

What is claimed is:

1. An imaging apparatus for imaging an object, the apparatus comprising:
   an enclosure chassis that defines an enclosed imaging volume and that provides an imaging aperture to a camera apparatus that mounts against the chassis and that further provides at least a first lateral access opening for access to the object;
   a platform having a light source that is energizable for illuminating the enclosed imaging volume through an illumination opening in the enclosure chassis; and
   a light-obstructing gasket that is coupled to the enclosure chassis and that has at least a first foldable lateral access leaf that folds to a first position against the first lateral access opening to block ambient light through the first lateral access opening and that folds away from the first lateral access opening to a second position to allow access to the object.

2. The imaging apparatus of claim 1 wherein the light-obstructing gasket further obstructs light entry between the enclosure chassis and the platform.

3. The imaging apparatus of claim 1 wherein the first foldable lateral access leaf lies against the platform when in the second position.

4. The imaging apparatus of claim 1 wherein the enclosure chassis further provides a second lateral access opening for access to the object and wherein the light-obstructing gasket further has a second foldable lateral access leaf that folds removably against and away from the second access opening.

5. The imaging apparatus of claim 4 wherein the second foldable lateral access leaf is bilaterally opposed to the first foldable lateral access leaf.

6. The imaging apparatus of claim 1 wherein the first foldable lateral access leaf is magnetically attracted to the first position against the first lateral access opening.

7. The imaging apparatus of claim 6 wherein the first foldable lateral access leaf further comprises one or more stiffener elements that are formed from a magnetic or from a ferromagnetic material.

8. The imaging apparatus of claim 1 further comprising one or more hinge elements that allow pivoting of the camera apparatus against or away from a surface of the enclosure chassis.

9. An imaging apparatus for imaging an object, the apparatus comprising:
   an enclosure chassis that defines an enclosed imaging volume and that provides an imaging aperture to a camera apparatus that mounts against the chassis at one or more hinge elements, wherein the hinge elements allow pivoting of the camera apparatus to a first position lying against a surface of the enclosure chassis or to a second position that is pivoted outward from the surface of the enclosure chassis, and wherein the enclosure chassis further provides at least a first access opening for access to the object, wherein the first access opening has a first repositionable cover for blocking ambient light.

10. The imaging apparatus of claim 9 wherein the enclosure chassis further comprises one or more illumination sources that are energizable for providing light to the object.

11. The imaging apparatus of claim 9 wherein the enclosure chassis further comprises at least first and second illumination sources that are energizable for providing light to the object and wherein the first and second illumination sources have substantially non-overlapping wavelength profiles.

12. The imaging apparatus of claim 11 further comprising at least one illumination status indicator that is indicative of an energized state of at least one of the at least first and second illumination sources and wherein the at least one indicator lies within the field of view of the camera apparatus at the imaging aperture.

13. The imaging apparatus of claim 11 wherein the first illumination source is an ultraviolet source.

14. The imaging apparatus of claim 13 wherein the second illumination source is a visible source.

15. The imaging apparatus of claim 14 further comprising a platform having a light source that is energizable for illuminating the enclosed imaging volume through an illumination opening in the enclosure chassis.

16. The imaging apparatus of claim 14 wherein the enclosure chassis further provides a second access opening for access to the object and wherein the second access opening has a second repositionable cover for blocking the ambient light.

17. The imaging apparatus of claim 16 wherein the second access opening is a lateral access opening.

18. The imaging apparatus of claim 17 wherein the second repositionable cover is bilaterally opposed to the first repositionable cover.

19. The imaging apparatus of claim 9 wherein the first access opening is a lateral access opening.

20. An imaging apparatus for imaging an object, the apparatus comprising:

an enclosure chassis that defines an enclosed imaging volume and that provides an imaging aperture to a camera apparatus that mounts against the chassis and that further provides at least a first lateral access opening for access to the object;

a repositionable cover that is coupled to the enclosure chassis and that has at least a first position against the first lateral access opening to block ambient light through the first lateral access opening and a second position to allow access to the object;

an illumination source that is energizable to provide illumination within the enclosure chassis;

and an illumination status indicator that is indicative of an energized state of the illumination source and wherein the at least one indicator lies within the field of view of the camera apparatus at the imaging aperture.

\* \* \* \* \*